(12) United States Patent
Bernstein et al.

(10) Patent No.: US 11,301,027 B2
(45) Date of Patent: *Apr. 12, 2022

(54) METHODS AND ARTICLES OF MANUFACTURE FOR HOSTING A SAFETY CRITICAL APPLICATION ON AN UNCONTROLLED DATA PROCESSING DEVICE

(71) Applicant: Abbott Diabetes Care Inc., Alameda, CA (US)

(72) Inventors: Daniel M. Bernstein, El Granada, CA (US); Saeed Nekoomaram, San Mateo, CA (US); Mark K. Sloan, Redwood City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/487,553

(22) Filed: Sep. 28, 2021

(65) Prior Publication Data

US 2022/0011851 A1    Jan. 13, 2022

Related U.S. Application Data

(63) Continuation of application No. 17/394,010, filed on Aug. 4, 2021, which is a continuation of application
(Continued)

(51) Int. Cl.
*G06F 1/00* (2006.01)
*G06F 11/30* (2006.01)
(Continued)

(52) U.S. Cl.
CPC .......... *G06F 1/3287* (2013.01); *G06F 1/3203* (2013.01); *G06F 8/61* (2013.01);
(Continued)

(58) Field of Classification Search
CPC .................................................... G06F 1/3287
See application file for complete search history.

(56) References Cited

U.S. PATENT DOCUMENTS

| 3,979,657 A | 9/1976 | Yorksie |
| 5,031,616 A | 7/1991 | Mann et al. |

(Continued)

FOREIGN PATENT DOCUMENTS

| CN | 101151513 A | 3/2008 |
| CN | 101369303 A | 2/2009 |

(Continued)

OTHER PUBLICATIONS

Extended European Search Report directed to related European Patent Application No. 21167794.3, dated Nov. 8, 2021; 9 pages.
(Continued)

*Primary Examiner* — Mohammed H Rehman
(74) *Attorney, Agent, or Firm* — Sterne, Kessler, Goldstein & Fox P.L.L.C.

(57) ABSTRACT

Methods and articles of manufacture for hosting a safety critical application on an uncontrolled data processing device are provided. Various checks and combinations of checks including installation, functional, host integrity, coexistence, interoperability, power management, and environment checks are performed at various times to determine if the safety critical application operates properly on the device. The operation of the SCA on the UDPD may be controlled accordingly.

20 Claims, 15 Drawing Sheets

Related U.S. Application Data

No. 16/272,300, filed on Feb. 11, 2019, now Pat. No. 11,099,627, which is a continuation of application No. 14/750,881, filed on Jun. 25, 2015, now Pat. No. 10,241,562, which is a continuation of application No. 14/739,976, filed on Jun. 15, 2015, now Pat. No. 9,519,333, which is a continuation of application No. 14/088,844, filed on Nov. 25, 2013, now Pat. No. 9,058,431, which is a continuation of application No. 12/876,840, filed on Sep. 7, 2010, now Pat. No. 8,601,465.

(60) Provisional application No. 61/359,265, filed on Jun. 28, 2010, provisional application No. 61/240,578, filed on Sep. 8, 2009.

(51) Int. Cl.

| | | |
|---|---|---|
| *G06F 1/3287* | (2019.01) | |
| *G06F 9/50* | (2006.01) | |
| *G06F 9/54* | (2006.01) | |
| *G06F 11/07* | (2006.01) | |
| *G16H 40/40* | (2018.01) | |
| *G06F 11/36* | (2006.01) | |
| *G06F 8/61* | (2018.01) | |
| *G06F 11/00* | (2006.01) | |
| *G06F 1/3203* | (2019.01) | |

(52) U.S. Cl.
CPC ............ *G06F 9/5011* (2013.01); *G06F 9/546* (2013.01); *G06F 11/004* (2013.01); *G06F 11/079* (2013.01); *G06F 11/0721* (2013.01); *G06F 11/0736* (2013.01); *G06F 11/0751* (2013.01); *G06F 11/3668* (2013.01); *G06F 11/3688* (2013.01); *G06F 11/3692* (2013.01); *G16H 40/40* (2018.01); *G06F 2201/865* (2013.01)

(56) References Cited

U.S. PATENT DOCUMENTS

| | | |
|---|---|---|
| 5,394,871 A | 3/1995 | Sauer et al. |
| 5,754,963 A | 5/1998 | Nunneley et al. |
| 6,035,421 A | 3/2000 | Henno et al. |
| 6,081,466 A | 6/2000 | McClure et al. |
| 6,110,228 A | 8/2000 | Albright et al. |
| 6,128,774 A | 10/2000 | Necula et al. |
| 6,272,674 B1 | 8/2001 | Holiday, Jr. |
| 6,285,298 B1 | 9/2001 | Gordon |
| 6,421,633 B1 | 7/2002 | Heinonen et al. |
| 6,490,722 B1 | 12/2002 | Barton et al. |
| 6,546,553 B1 | 4/2003 | Hunt |
| 6,604,237 B1 | 8/2003 | Giammaria |
| 6,640,334 B1 | 10/2003 | Rasmussen |
| 6,745,385 B1 | 6/2004 | Lupu et al. |
| 6,807,641 B1 | 10/2004 | Ishiguro et al. |
| 6,830,180 B2 | 12/2004 | Walsh |
| 7,041,468 B2 | 5/2006 | Drucker et al. |
| 7,152,092 B2 | 12/2006 | Beams et al. |
| 7,191,208 B1 | 3/2007 | Achtermann et al. |
| 7,251,812 B1 | 7/2007 | Jhanwar et al. |
| 7,254,608 B2 | 8/2007 | Yeager et al. |
| 7,266,819 B2 | 9/2007 | Helgesen et al. |
| 7,308,300 B2 | 12/2007 | Toews et al. |
| 7,322,028 B2 | 1/2008 | Belovich |
| 7,334,226 B2 | 2/2008 | Ramachandran et al. |
| 7,343,364 B2 | 3/2008 | Bram et al. |
| 7,353,509 B2 | 4/2008 | Sheehy |
| 7,467,093 B1 | 12/2008 | Newton et al. |
| 7,509,156 B2 | 3/2009 | Flanders |
| 7,596,784 B2 | 9/2009 | Abrams et al. |
| 7,682,351 B2 | 3/2010 | Aoki |
| 7,689,985 B2 | 3/2010 | Callender |
| 7,703,093 B2 | 4/2010 | Fischer et al. |
| 7,867,165 B2 | 1/2011 | Brown |
| 7,972,267 B2 | 7/2011 | Brown |
| 7,996,245 B2 | 8/2011 | Gejdos et al. |
| 8,086,665 B1 | 12/2011 | Soukup et al. |
| 8,103,718 B2 | 1/2012 | O'Shea et al. |
| 8,184,969 B2 | 5/2012 | Guthrie et al. |
| 8,204,729 B2 | 6/2012 | Sher |
| 8,224,669 B2 | 7/2012 | Peterka et al. |
| 8,234,639 B2 | 7/2012 | Ramachandran et al. |
| 8,296,043 B2 | 10/2012 | Mueller et al. |
| 8,296,756 B1 | 10/2012 | Feeser et al. |
| 8,323,189 B2 | 12/2012 | Tran |
| 8,370,835 B2 | 2/2013 | Dittmer |
| 8,418,172 B2 | 4/2013 | Addington et al. |
| 8,475,739 B2 | 7/2013 | Holmes et al. |
| 8,533,253 B2 | 9/2013 | McCoy |
| 8,554,953 B1 | 10/2013 | Sorensen et al. |
| 8,555,070 B2 | 10/2013 | Claus et al. |
| 8,562,587 B2 | 10/2013 | Kovatchev |
| 8,566,818 B2 | 10/2013 | Young |
| 8,576,191 B2 | 11/2013 | Knott et al. |
| 8,578,370 B2 | 11/2013 | Dai et al. |
| 8,601,465 B2 | 12/2013 | Bernstein et al. |
| 8,615,752 B2 | 12/2013 | Izard et al. |
| 8,621,049 B2 | 12/2013 | Ebrom et al. |
| 8,628,512 B2 | 1/2014 | Kochanek et al. |
| 8,726,266 B2 | 5/2014 | Kiale |
| 8,732,693 B2 | 5/2014 | Mitusya et al. |
| 8,813,061 B2 | 8/2014 | Hoffman et al. |
| 8,862,448 B2 | 10/2014 | Holmes et al. |
| 8,893,120 B2 | 11/2014 | Pinsky et al. |
| 8,935,691 B2 | 1/2015 | Ben Ayed |
| 8,954,373 B2 | 2/2015 | Atlas |
| 8,978,027 B2 | 3/2015 | Haemel et al. |
| 9,010,477 B2 | 4/2015 | Saettel et al. |
| 9,015,698 B2 | 4/2015 | Bernstein et al. |
| 9,058,431 B2 | 6/2015 | Bernstein et al. |
| 9,122,775 B2 | 9/2015 | Schunder |
| 9,124,635 B2 | 9/2015 | Robinson et al. |
| 9,177,153 B1 | 11/2015 | Perrig et al. |
| 9,218,453 B2 | 12/2015 | Groll |
| 9,326,709 B2 | 5/2016 | Budiman |
| 9,519,333 B2 | 12/2016 | Bernstein et al. |
| 9,519,334 B2 | 12/2016 | Bernstein et al. |
| 9,519,335 B2 | 12/2016 | Bernstein et al. |
| 9,529,414 B2 | 12/2016 | Bernstein et al. |
| 9,552,052 B2 | 1/2017 | Bernstein et al. |
| 9,619,013 B2 | 4/2017 | Bernstein et al. |
| 10,241,562 B2 | 3/2019 | Bernstein et al. |
| 11,099,627 B2 | 8/2021 | Bernstein et al. |
| 2002/0023852 A1* | 2/2002 | Mcivor ............... A61B 5/6849 206/305 |
| 2004/0140904 A1 | 7/2004 | Bertness |
| 2004/0245534 A1 | 12/2004 | Yamada |
| 2005/0088147 A1 | 4/2005 | Svensson et al. |
| 2006/0111156 A1 | 5/2006 | Choi et al. |
| 2006/0178570 A1 | 8/2006 | Robinson et al. |
| 2006/0181822 A1 | 8/2006 | Rana |
| 2006/0229772 A1 | 10/2006 | McClary |
| 2006/0230398 A1 | 10/2006 | Yokota |
| 2006/0277218 A1 | 12/2006 | Franco et al. |
| 2007/0022328 A1 | 1/2007 | Tarra et al. |
| 2007/0266177 A1 | 11/2007 | Vismans et al. |
| 2008/0110236 A1 | 5/2008 | Hajishah et al. |
| 2008/0122796 A1 | 5/2008 | Jobs et al. |
| 2008/0127175 A1 | 5/2008 | Naranjo et al. |
| 2008/0172665 A1 | 7/2008 | McIlroy |
| 2008/0183502 A1* | 7/2008 | Dicks ..................... G16H 40/67 705/2 |
| 2008/0234562 A1 | 9/2008 | Jina |
| 2008/0315793 A1 | 12/2008 | Sanchez |
| 2009/0120810 A1 | 5/2009 | Phan et al. |
| 2009/0164838 A1 | 6/2009 | Haller |
| 2009/0234465 A1 | 9/2009 | Korsten |
| 2010/0069730 A1* | 3/2010 | Bergstrom ............ G16H 15/00 600/365 |
| 2010/0214813 A1 | 8/2010 | Choi et al. |

(56) References Cited

U.S. PATENT DOCUMENTS

2010/0242034 A1  9/2010  Rugh et al.
2011/0004084 A1  1/2011  Feldman et al.
2011/0126188 A1  5/2011  Bernstein et al.
2013/0132010 A1  5/2013  Winger et al.
2014/0075246 A1  3/2014  Bernstein et al.
2014/0082607 A1  3/2014  Bernstein et al.
2015/0164391 A1  6/2015  Hernandez-Rosas et al.
2015/0277999 A1  10/2015  Bernstein et al.
2015/0286562 A1  10/2015  Bernstein et al.
2015/0293584 A1  10/2015  Bernstein et al.
2015/0293803 A1  10/2015  Bernstein et al.
2015/0293804 A1  10/2015  Bernstein et al.
2015/0293805 A1  10/2015  Bernstein et al.
2015/0317186 A1  11/2015  Bernstein et al.
2016/0073349 A1  3/2016  Mohan et al.
2016/0282896 A1  9/2016  Edwards et al.
2019/0179401 A1  6/2019  Bernstein et al.
2021/0365102 A1  11/2021  Bernstein et al.

FOREIGN PATENT DOCUMENTS

DE   1008003531       7/2009
EP      1224543 B1    2/2009
WO   20100091102 A1   8/2010

OTHER PUBLICATIONS

Walters, R. A. et al., "Software Safety Techniques for Implantable Medical Devices," Proceedings of the Annual International Conference of the Engineering in Medicine and Biology Society. Paris, Oct. 29-Nov. 1, 1992; [Proceedings of the Annual International Conference of the Engineering in Medicine and Biology Society] New York, I, vol. 14, part 03, Oct. 29, 1992, p. 965/966.
Communication Pursuant to Article 94(3) EPC dated Jan. 22, 2018, regarding European Patent Application No. 10815970.8.
Extended European Search Report directed to related European Patent Application No. 21194269.3, dated Dec. 22, 2021; 10 pages.

* cited by examiner

METHODS AND ARTICLES OF MANUFACTURE FOR HOSTING A SAFETY CRITICAL APPLICATION ON AN UNCONTROLLED DATA PROCESSING DEVICE

BACKGROUND

Safety critical systems are systems whose failures or malfunctions may result in significantly detrimental consequences such as death or injury to persons, severe damage or loss to equipment or to environment. Because safety critical systems have potentially dangerous consequences, the entire system undergoes a verification and validation processes to provide a certain level of confidence that the entire system operates properly and will continue to operate properly for all approved-for-use conditions.

Medical systems are an example of safety critical systems that require a certain level of confidence that the system will operate and continue to operate properly. Medical systems may detrimentally affect a user's health and well-being if not operating properly or not known to be operating properly. This is especially true for medical systems that provide user with health-related diagnostic or therapeutic information. For example, analyte monitoring devices, such as glucose meters, provide users with diagnostic information about their blood-sugar levels. Inaccuracies or significant delays in reporting such diagnostic information may potentially lead to injury or death of a user. Furthermore, as another example, medical systems may provide users with therapeutic information such as recommended medication dosages. For instance, glucose meters may provide users with recommended insulin dosages in response to a glucose measurement in order to remedy the current or anticipated blood sugar levels. Inaccuracies or significant delays in reporting such therapeutic information may potentially lead to injury or death of the user.

Once the entire safety critical system have been verified and validated, the entire system is released and is not expected to undergo software and/or hardware changes. This provides for a very controlled system environment. New software and/or hardware changes are not introduced into the market unless and until the new hardware and/or software have undergone a new validation process. Such a controlled system environment provides a certain level of confidence that the system will not be altered or changed and potentially affects the proper operation of the system.

However, when a safety critical application (SCA) is installed on an uncontrolled data processing device (UDPD) that permits hardware and/or software changes by the user, any changes to the UDPD may detrimentally affect the proper operation of the SCA on the UDPD. UDPDs generally permit the user to make software and/or hardware changes to the device—e.g., installing/removing software programs, installing/removing drivers, adding/removing hardware components, etc. Example UDPDs may include, personal computers (e.g., desktop, notebook, etc.), mobile phones (e.g., iPhones®, Blackberry®, etc.), personal digital assistants (PDAs), etc. Thus, the uncontrolled nature of the data processing devices compromises any assurance that the SCA will operate, or continue to operate, properly on the UDPD.

SUMMARY

Methods and articles of manufacture for hosting safety critical applications on uncontrolled data processing devices are provided. Various combinations of checks (e.g., installation check, functional check, host integrity check, coexistence check, interoperability check, power management check, environment check, etc.) are executed at various times to determine if the SCA may operate properly on the device. The operation of the SCA on the UDPD may be controlled accordingly.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Before the present inventions are described, it is to be understood that this invention is not limited to particular aspects described, as such may, of course, vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a firmware update" includes a plurality of such firmware updates and reference to "the firmware update" includes reference to one or more firmware updates and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
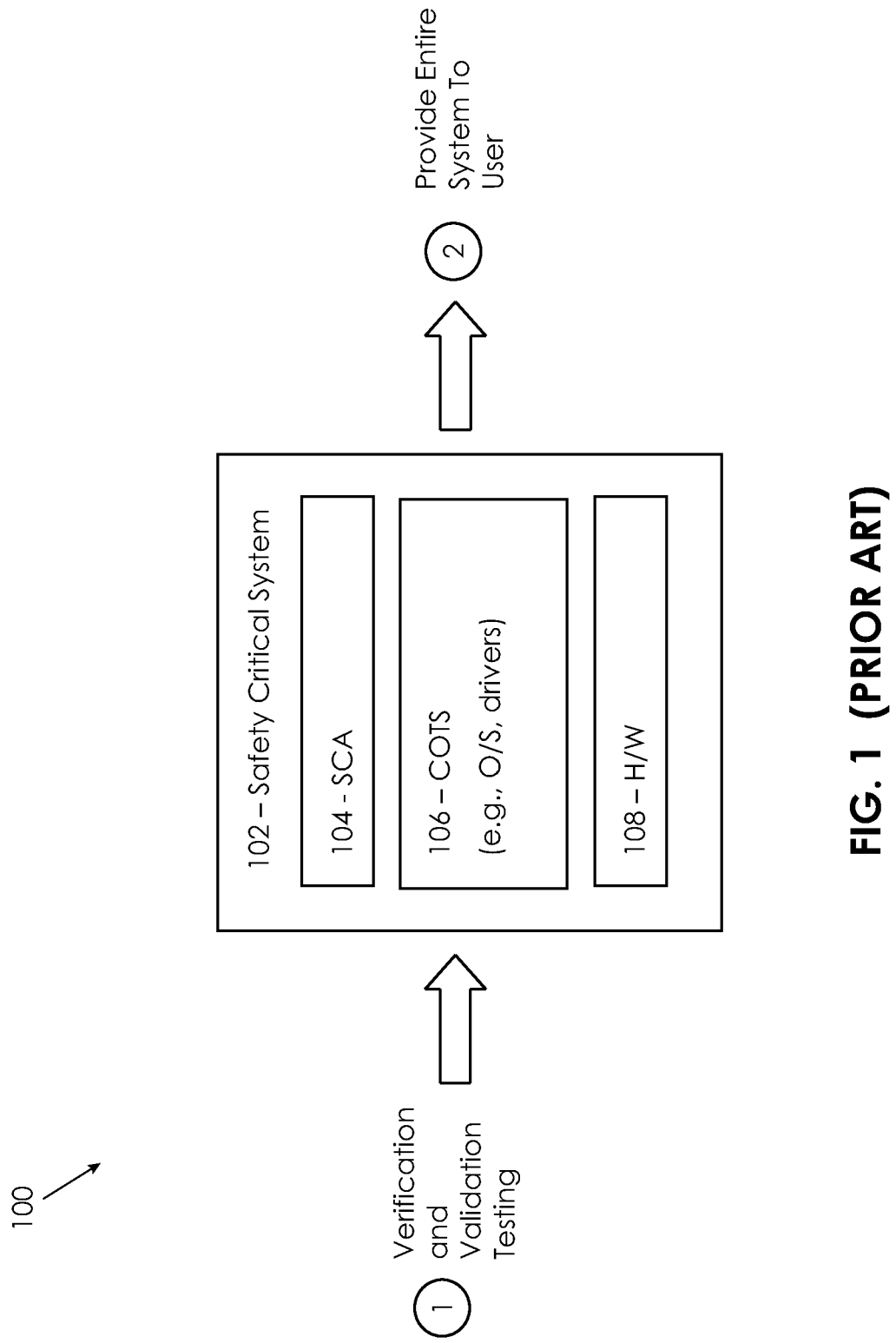
FIG. 1 illustrates a flow diagram for a method of verification and validation for safety critical systems, according to the prior art.

FIG. 1 illustrates a flow diagram for a method of verification and validation for safety critical systems, according to the prior art. As shown, safety critical system 102 is a dedicated system comprising a safety critical application 104, commercial off-the-shelf software components 106 (e.g., operating systems, drivers, etc.), and various hardware components 108. Verification and validation process 100 is performed on the entire dedicated system 102. After the initial verification and validation is complete, the entire dedicated system 102 is provided to the user. The user is able to use the safety critical system 102 for its intended purpose but cannot make system changes, such as making changes to the operating system, modifying the application program, installing or removing drivers, installing or removing software programs, making any significant hardware changes, etc. This controlled environment provides the manufacturer and user with a certain level of confidence that the entire dedicated safety critical system 102 not only operates properly, but will not be subsequently altered or changed such that it does not operate properly in the future.

More and more people today, however, have access to one or more UDPDs. UDPDs have become an integral part of many people's lives and provide people with continual and convenient access to various applications to be used on these devices. For example, many people today have a desktop or laptop computer, as well as mobile phone, that they can download various applications to and use on the specific device. The more accessible the devices are to the user, the more convenient they become. While SCAs may be verified and validated before distribution to users, when loaded onto a UDPD, any assurance that the SCA will operate properly is compromised because of the uncontrolled nature of the UDPD.

Figure 2:
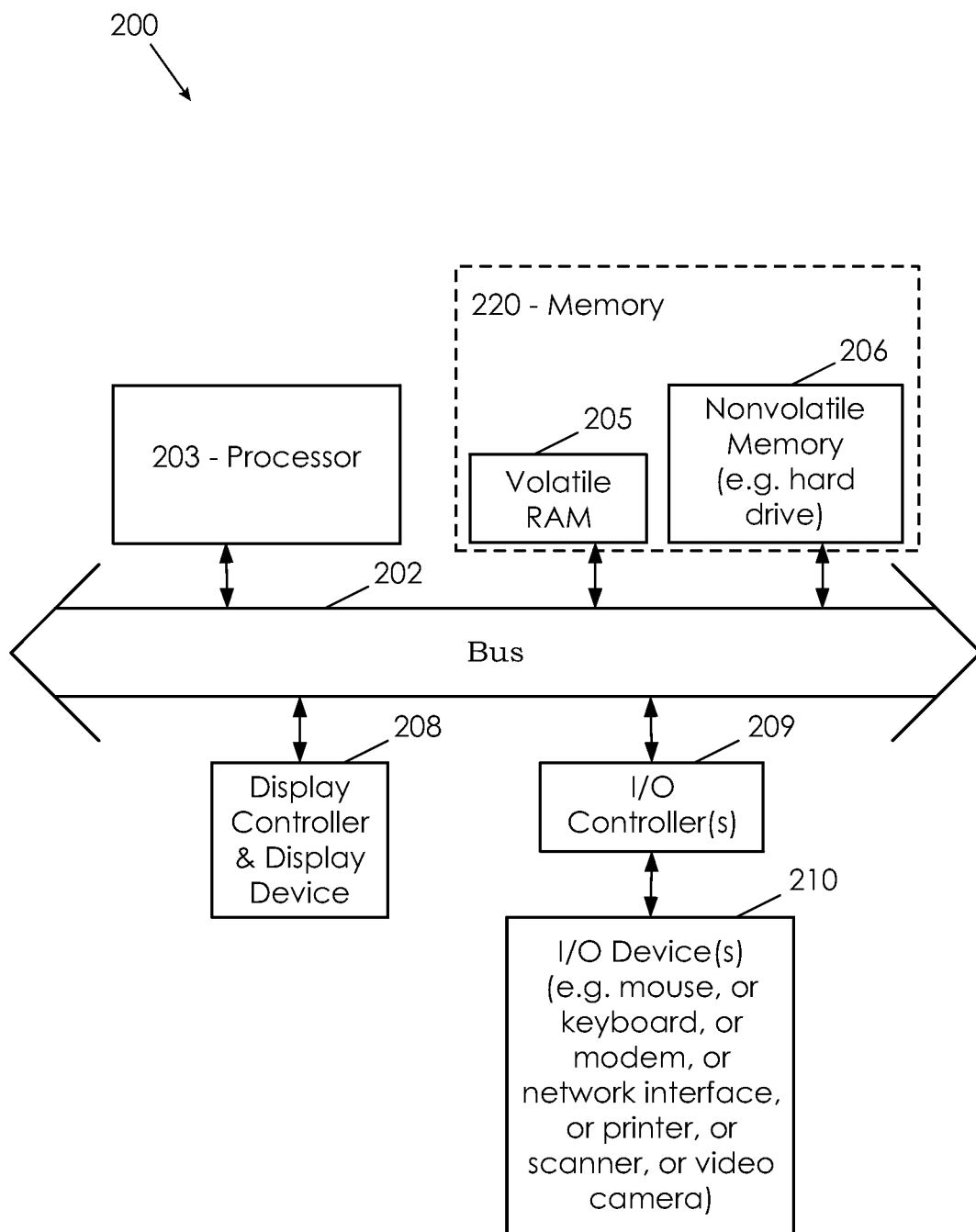
FIG. 2 illustrates a high level block diagram of an example uncontrolled data processing system, according to the prior art.

FIG. 2 illustrates a high level block diagram of an example uncontrolled data processing system, according to the prior art. As shown in FIG. 2, UDPD 200 includes a system bus 202 which is coupled to processor 203, volatile memory 205, and non-volatile memory 206. The term processor is used herein to generally refer to any processing element such as a microprocessor, microcontroller, digital signal processor, etc. Volatile memory 205 may include random access memory (RAM), for example, and/or any other type of memory that requires power continually in order to refresh or maintain the data in the memory. Non-volatile memory 206 may include, for example, read-only memory (ROM), flash memory, electronic or magnetic or optical drives, and/or any other type of memory which maintains data even after power is removed from the system. While only a single block is shown for each, it should be understood that one or more processors, volatile memory, or nonvolatile memory may be implemented. Moreover, memory 220 is represented by dotted lines and refers generally to any available memory or other machine-readable media that can be accessed by processor 202. As such, memory 220 is shown generally to comprise volatile memory 205 and nonvolatile memory 206.

Memory 220 is coupled to processor 203 via system bus 202 and stores instruction sets to be executed by processor 203. Processor 203, in turn comprises processing elements and/or logic circuitry to execute the instructions sets. System bus 202 interconnects these various components together and also interconnects components 203, 205, and 206, to a display controller and display device 208, and to peripheral devices such as input/output (I/O) devices 210, such as numeric keypads, keyboards, modems, network interfaces, printers, scanners, video cameras and other devices which are well known in the art. In some instances, the I/O devices 210 are coupled to the system bus 202 through input/output controllers 209. System bus 202 may include one or more buses connected to each other through various bridges, controllers and/or adapters (not shown) as is well known in the art. In some instances, the I/O controller 209 includes a USB (Universal Serial Bus) adapter for controlling USB peripherals, and/or an IEEE-1394 bus adapter for controlling IEEE-1394 peripherals.

While FIG. 2 shows that non-volatile memory 206 is a local device coupled directly to the rest of the components in the UDPD, it will be appreciated that in some instances the non-volatile memory may be remote from the system, such as a network storage device coupled to UDPD 200 through a wired and/or wireless network via a network interface, or other suitable remote storage device. Furthermore, it will be appreciated that the various embodiments described herein may be implemented with UDPDs which have more or fewer components than UDPD 200.

UDPDs such as the one described above may have stored therein, an operating system and other software programs (e.g., in Flash memory, hard drive, etc.). The programs may be initially provided in a variety of ways to the UDPD—e.g., in manufacturing, through a remote connection (e.g., via a network interface to a remote location over a network), by a removable storage device (e.g., memory card, CD-ROM, etc.), etc. The programs and applications described herein comprise a set of instructions that are executed by the processor.

Programs are provided to the UDPD and are generally stored in nonvolatile memory such as (Flash memory, hard drive, etc.). In some instances, when the programs are to be run on the UDPD, the programs are loaded into volatile memory (e.g., RAM) and accessed by the processor to be executed.

In some aspects, the UDPD may include a processor which implements an application programming interface (API) for running instruction sets or software program. The API may include the ability for an instruction set to interrupt other instruction sets, and to control the presentation of data from another device (e.g., a medical device such as an analyte monitoring device and/or drug administration device) on various outputs (e.g., audio, visual, and tactile outputs) on the UDPD.

When a SCA is installed on a UDPD, there are no assurances that the SCA will operate properly on the UDPD because there has been no verification or validation process performed after the SCA is installed on the UDPD. The environment of the UDPD is dynamic and can change in a way that effects the proper operation of the SCA on the UDPD. For example, various software programs and drivers may be installed and removed from the UDPD and not only change the processing environment of the UDPD, but also may consume processing bandwidth making the UDPD process other applications more slowly. Various software configurations may be changed as well, which may affect the processing environment of the UDPD. Furthermore, changes to hardware components (e.g., wireless cards/modems, etc.), or configurations thereof, may affect the proper operation of the SCA on the UDPD (e.g., prevent communication to an external device). Still further, activities of the user may lead to the system obtaining viruses or spyware that can change the environment of the UDPD or consume processing bandwidth and prevent the SCA from operating properly. Moreover, changes to the system may impact power consumption of the system which may compromise the SCA. Thus, the uncontrolled nature of the data processing devices compromises any assurance that the SCA will operate or continue to operate properly on the UDPD.

In some aspects of the present disclosure, methods and article of manufactures for hosting a safety critical application on an uncontrolled data processing device are provided. Various combinations of checks (e.g., installation check, functional check, host integrity check, coexistence check, interoperability check, power management check, environment check, etc.) may be executed at various times to determine if the SCA may operate properly on the device, and the operation of the SCA on the UDPD may be controlled accordingly.

In some aspects of the present disclosure, a test harness module (also referred to herein as "test harness") is provided that comprises one or more checks used to determine whether the SCA operates properly on the UDPD and to control the operation of the SCA on the UDPD accordingly. Example checks that the test harness may include, but not limited to, are an installation check, functional check, host integrity check, coexistence check, interoperability check, power management check, environment check. The methods and functions related to each are described in further detail throughout the present disclosure.

Figure 3:
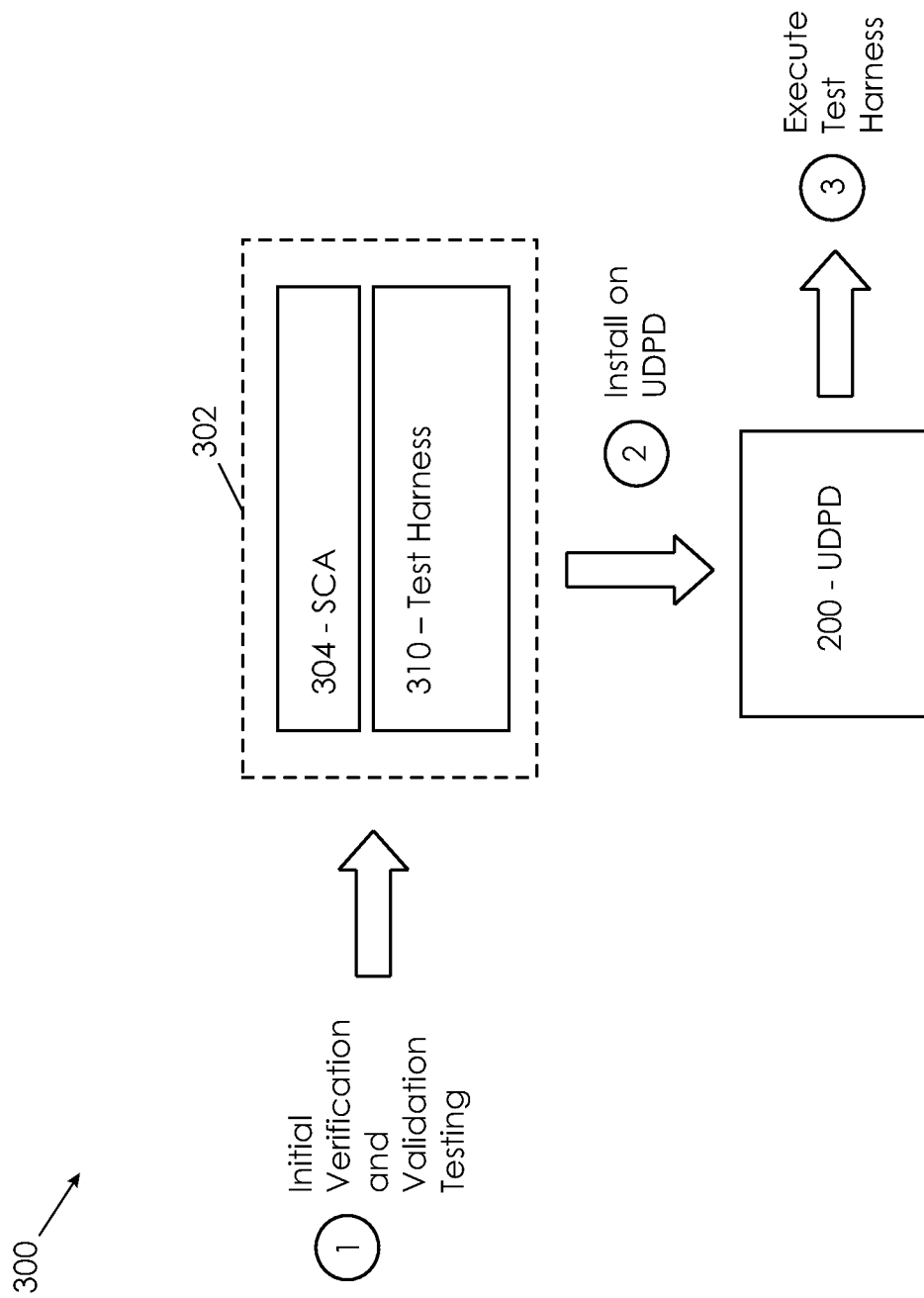
FIG. 3 illustrates a flow diagram for a method of verification and validation, according to some aspects of the present disclosure.

FIG. 3 illustrates a flow diagram for a method of verification and validation, according to some aspects of the present disclosure. As shown, verification and validation process 300 begins with an initial verification and validation performed on a SCA 304 and test harness 310 to ensure that both successfully pass verification and validation, as represented by reference circle number one in FIG. 3. The initial verification and validation is performed by the manufacturer of SCA 304 and test harness 310, for example, before SCA 304 and test harness 310 are distributed to users.

In some instances, SCA 304 and test harness 310 may be verified and validated together at the same time, as shown. In some instances, SCA 304 and test harness 310 may be separately verified and validated, and further may be verified and validated at different times (e.g., when a new version of either is implemented, etc.). It should be appreciated that while the test harness is described herein as a single test harness, it is contemplated that one or more of the checks may be provided by one or more test harnesses on the same or different computer readable media. Further, each test harness may be verified and validated at different times in some instances.

It should also be appreciated that SCA 304 described herein may be associated with a wide range of safety critical applications. In some aspects of the present disclosure, SCA 304 is a medically-related application. For example, SCA 304 may provide a user with health-related tools/features (e.g., information, computations, communications, etc.) associated with diagnosis, therapy and treatment, drug administration and dosage, data management (e.g., logs, records, history, graphs, charts, reports, etc.), etc.

In some aspects of the present disclosure, SCA 304 is an application associated with analyte monitoring and/or determination. Example features of SCA 304 may include, for example, one or more of the following: determining analyte amounts or concentrations from a sample (e.g., saliva, blood, other bodily fluid, etc.); receiving measurement data; managing and/or processing measurement data (e.g., logging measurements, providing warnings based on measurement values, providing alternative representations of data in the form of reports, graphs, charts, etc.); calculating drug dosage amounts (e.g., insulin bolus calculations) based on measurement data, exercise data, food intake, etc.; communicating with a remote device external to UDPD 200 (e.g., communicating drug dosage and/or administration data to a medication delivery device such as an insulin pump; receiving measurement data from a continuous in vivo monitoring device such as an implanted sensor; communicating with an analyte meter; etc.); other analyte monitoring feature described herein; etc. It should be appreciated that the above features listed are exemplary and that other features associated with analyte monitoring and/or determining may be implemented. In some aspects of the present disclosure, SCA 304 may be associated with glucose monitoring and/or determination. In some aspects of the present disclosure, SCA 304 may be associated with ketone monitoring and/or determination. Additional example applications related to analyte monitoring are provided in international patent application no. PCT/US2010/23076, entitled, "Multi-Function Analyte Test Device and Methods Therefor", the entirety of which is incorporated herein by reference for all purposes.

After the initial verification and validation, SCA 304 and test harness 310 are installed on a UDPD 200, as represented by reference circle number two. For example, the user may download SCA 304 and test harness 310 via the internet, removable storage device (e.g., FLASH memory card, CD-ROM, etc.), or any other suitable machine-readable media, connection, or method. In some aspects of the present disclosure, an article of manufacture is provided that comprises machine-readable medium that has various checks stored thereon as machine-executable instructions. For instance, the machine readable medium may have test harness stored therein and in some instances SCA as well.

As mentioned before, example UDPDs may include, personal computers (e.g., desktop, notebook, etc.), mobile phones (e.g., iPhones®, Blackberry®, etc.), personal digital assistants (PDAs), digital music player (e.g., iPod®), etc. Additional information and details for some example uncontrolled data processing devices (e.g, iPhone®) are described in US Patent Application Publication No. US2008/0122796 published May 29, 2008 titled "Touch Screen Device, Method, and Graphical User Interface for Determining Commands by Applying Heuristics", the entirety of which is incorporated herein by reference for all purposes. In some aspects of the present disclosure a UDPD is provided that includes a processor and memory operably coupled to the processor, wherein the memory has instructions stored therein to host the SCA on the UDPD. The memory may include instructions for one or more of the various checks described herein. For instance, the memory may have test harness stored therein to perform the various checks on the SCA.

In some aspects of the present disclosure, an analyte monitoring system is provided that includes a UDPD having a processor and memory operably coupled to the processor, wherein the memory has instructions stored therein to host the SCA on the UDPD. The memory may include instructions for one or more of the various checks described herein. For instances, the memory may have test harness stored therein to perform the various checks on the SCA.

In some aspects of the present disclosure, the analyte monitoring system may include, in addition to the UDPD, an element having a sensor for providing measurement data from an analyte sample. The element is in communication with the UDPD and provides the measurement data to the UDPD. It should be appreciated that the element may communicate with the UDPD via a wireless or wired connection using any variety of wired or wireless technology. In some instances, the element may be an implanted or on-body analyte sensor. In some instances, the element may include a strip port for receiving an analyte sample—e.g., via a test strip or other in-vitro application. In some instances, the element may be an adapter that removably couples to the UDPD.

SCA 304 and test harness 310 may be installed on UDPDs communicating with elements (e.g., adapters) and/or modules that provide additional functionality to a UDPD running a SCA. Examples and additional information of adapters used with UDPDs are described in U.S. provisional application No. 61/325,021 titled "Mobile Phone Display for Continuous Analyte Monitoring", the entirety of which is incorporated herein by reference for all purposes. Also, examples of analyte monitoring modules used with UDPDs are described in U.S. Pat. No. 7,041,468 issued on May 9, 2006 titled "Blood Glucose Tracking Apparatus and Method" and in US Patent Application Publication No. US2004/0245534 published Dec. 16, 2004 titled "Glucose Measuring Module and Insulin Pump Combination", the entireties of which are incorporated herein by reference for all purposes.

SCA 304 and test harness 310 may also be installed on a modular analyte monitoring devices when one or more modules are unprotected. Modular analyte monitoring devices includes a base module and at least one other module that removably couples to the base module to form a single integrated analyte monitoring device. In this way, various modules with different features may be coupled to the base module and provide the base module with those corresponding features. If, for example, the base module is a UDPD that allows the user to download and/or remove software programs, test harness 310 may be installed on the base module to provide some level of assurance that the SCA installed on the base module may operate properly on the base module. Examples and additional information on modular meters are described in U.S. provisional patent application No. 61/325,155, titled, "Modular Analyte Monitoring Device", the entirety of which is incorporated herein by reference for all purposes.

Figure 17A:
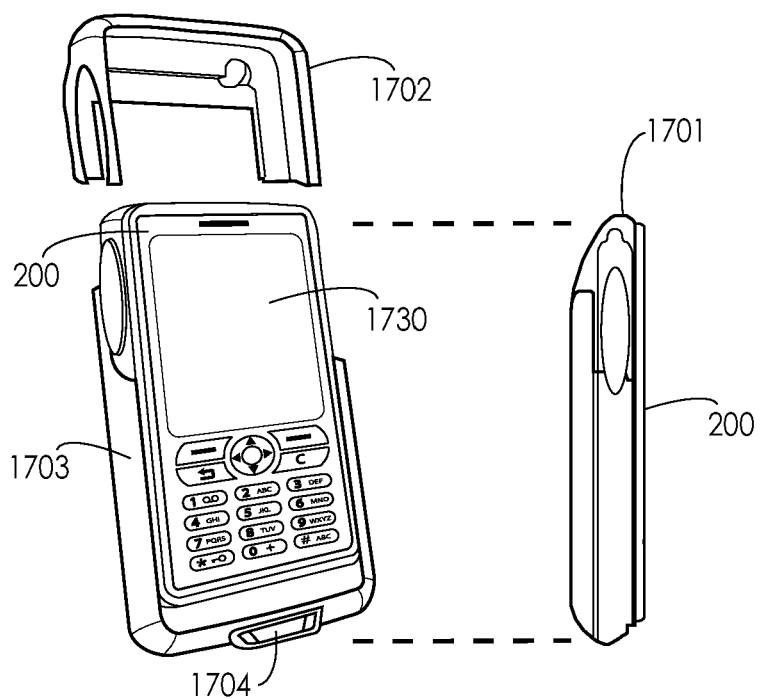
FIGS. 17A and 17B illustrate an adapter, including an analyte monitoring device, removably coupled to, and in communication with, a UDPD running a SCA, according to some aspects of the present disclosure.
Figure 17B:
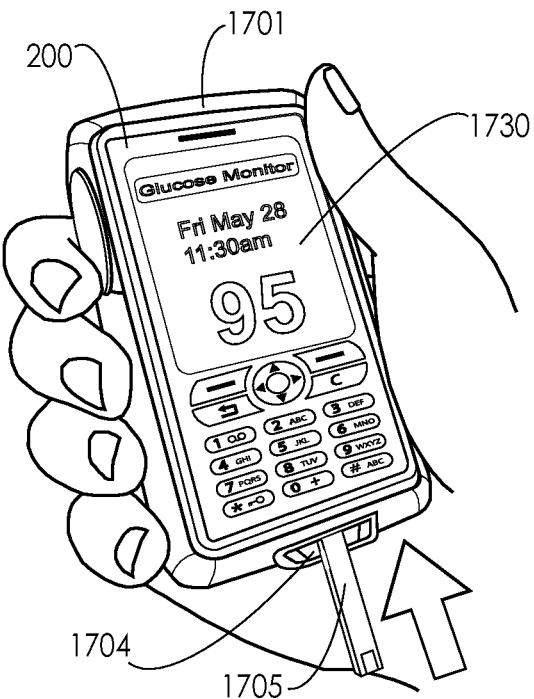

FIGS. 17A-B and 18A-B illustrate example UDPDs that couple with adapters to acquire additional analyte monitoring capabilities and which may have SCA 304 and test harness 310 installed thereon, according to some aspects of the present disclosure. FIGS. 17A and 17B illustrate an adapter including an analyte monitoring device, removably coupled to and in communication with a UDPD running a SCA. FIG. 17A illustrates a partially exploded perspective view, as well as a side view, of adapter 1701 removably coupled to a UDPD 200. FIG. 17B illustrates a perspective view of adapter 1701 removably coupled to UDPD 200.

Adapter 1701 is shown comprising two pieces 1702 and 1703 that engage to form the adapter and permit the adapter 1701 to be securely coupled to, and removed from, UDPD 200. UDPD 200 is shown in this exemplary example as a mobile phone. It should be understood that UDPD 200 may be any variety of uncontrolled data processing devices—e.g., a PDA, mobile phone (e.g., cellular phone), etc. Such devices include for example, BlackBerry®, iPhone®, iPod®, iPod Touch® devices, etc.

Adapter 1701 is configured to communicate with UDPD 200. In some instances, adapter 1701 may include a wireless communication module and communicate with UDPD 200 via wireless communication—e.g., via Bluetooth, infrared, or other wireless technology. In some instances, adapter 1701 may include a communication connector that communicates with UDPD 200 via a wired connection—e.g., via a micro-USB port, or other communication connection, on UDPD 200.

Adapter 1701 includes strip port 1704 and associated circuitry for receiving a sample for an analyte measurement. UDPD 200 has SCA 304 stored within memory for execution by UDPD 200. SCA 304 is an analyte monitoring application which provides UDPD 200 with analyte monitoring capabilities. Depending on the specific application implemented, one or more analytes such as glucose, ketone, etc., may be monitored.

SCA 304 and UDPD 200 is in communication with adapter 1701 and uses the test strip port 1704 to receive a test strip 1705 and perform a measurement on the sample provided. For example, as shown in FIG. 17B, test strip 1705 is inserted into strip port 1704 provided by adapter 1701. SCA 304 processes data from the test strip 1705 and obtains a measurement reading using the processor of UDPD 200. SCA 304 then conveys the measurement reading to the user via a display 1730 on UDPD 200. It should be appreciated that additional monitoring capabilities may also be performed by SCA 304 running on UDPD 200, such as those described herein—e.g., audibly outputting the measurement reading, logging the measurement data, providing alarms, calculating medication dosages, communicating with medication delivery devices, etc.

UDPD 200 also has test harness 310 (and any other additional checks implemented that are not necessarily part of test harness) stored in memory and as described herein executes various checks to achieve a certain level of confidence that the SCA 304 may operate properly on UDPD 200. Also, as described herein, the various checks may be initiated in various combinations and at different times as desired.

In some embodiments, adapter 1701 may be configured to perform the analyte measurement (e.g., via an on-board processor) and communicates the measurement reading to UDPD 200 via the wired or wireless connection with UDPD 200. UDPD 200 runs SCA 304 and communicates with adapter 1701 to receive the measurement readings and provides additional monitoring capabilities such as those described herein—e.g., displaying and/or outputting audibly the measurement reading, logging the measurement data, providing alarms, calculating medication dosages, communicating with medication delivery devices, etc.

Figure 18A:
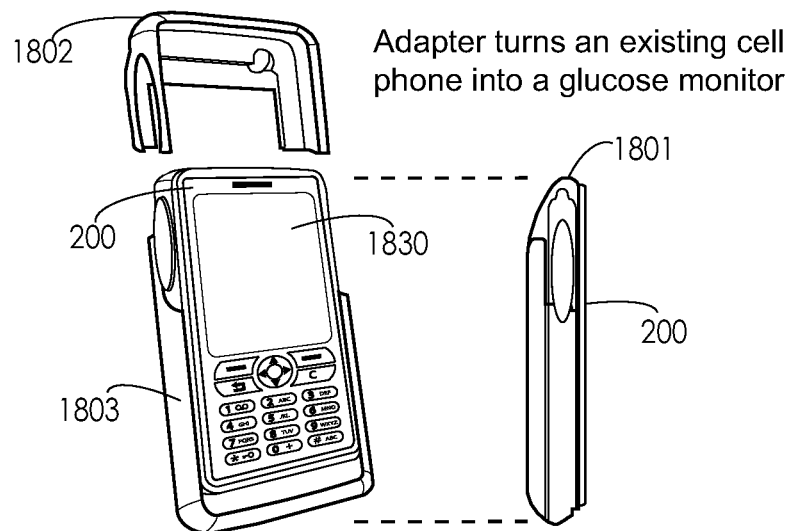
FIGS. 18A and 18B illustrate an adapter, including an analyte monitoring device, removably coupled to, and in communication with, a UDPD running a SCA, according to some aspects of the present disclosure.
Figure 18B:
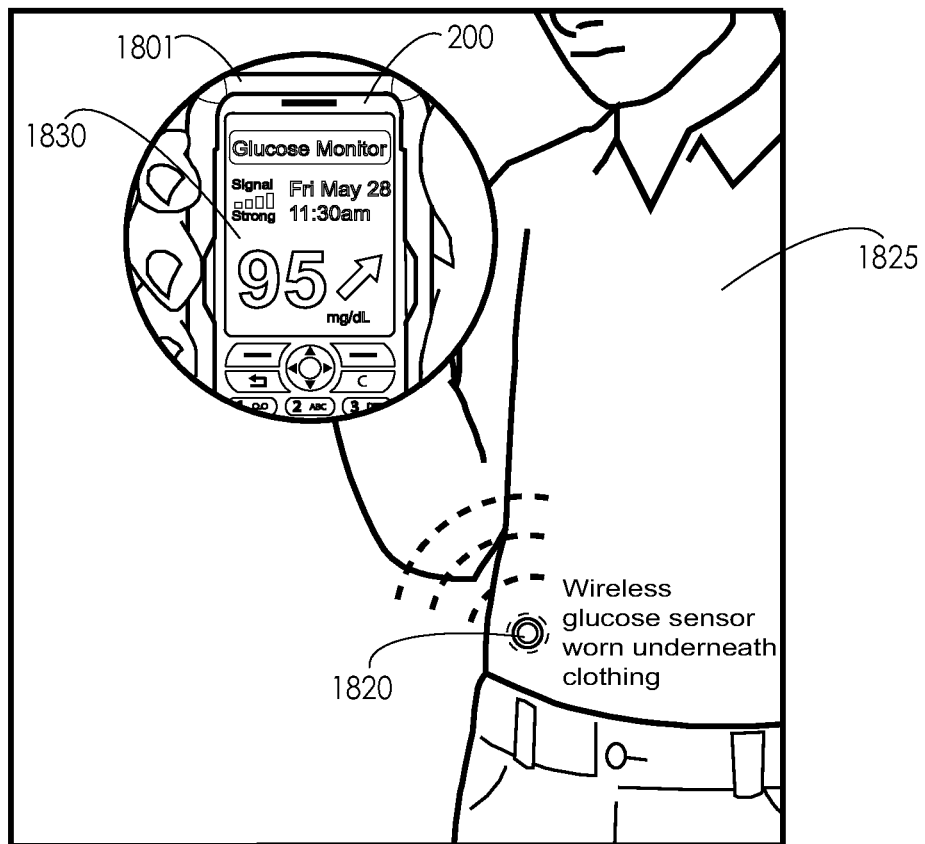

FIGS. 18A and 18B illustrate an adapter including an analyte monitoring device, removably coupled to and in communication with a UDPD running a SCA. FIG. 18A illustrates a partially exploded perspective view, as well as a side view, of adapter 1801 removably coupled to UDPD 200. FIG. 18B illustrates a perspective view of adapter 1801 removably coupled to UDPD 200. Adapter 1801 enables UDPD 200 to communicate with a remote device.

Adapter 1801 is shown comprising two pieces 1802 and 1803 that engage to form the adapter and permit the adapter 1801 to be securely coupled to, and removed from, UDPD 200. UDPD 200 is shown in this exemplary embodiment as a mobile phone. It should be understood that UDPD 200 may be any variety of uncontrolled data processing devices—e.g., a PDA, mobile phone (e.g., cellular phone), etc. Such devices include for example, BlackBerry®, iPhone®, iPod®, iTouch® devices, etc.

Adapter 1801 is configured to communicate with UDPD 200. In some instances, adapter 1801 may include a wireless communication module and communicate with UDPD 200 via wireless communication—e.g., via Bluetooth, infrared, or other wireless technology. In some instances, adapter 1801 may include a communication connector that communicates with UDPD 200 via a wired connection—e.g., via a micro-USB port, or other communication connection, on UDPD 200. Adapter 1801 also communicates with remote sensor device 1820 via a wireless communication module, as shown in FIG. 18B. Remote sensor device 1820 is shown as an on-body analyte sensor (e.g., an implanted or partially implanted analyte sensor) on user 1825. Remote sensor device 1820 may be, for example, an implanted or partially implanted glucose sensor for continuous glucose measurement (CGM) or glucose on demand (God) applications.

UDPD 200 has SCA 304 stored within memory for execution by UDPD 200. SCA 304 is an analyte monitoring application which provides UDPD 200 with analyte monitoring capabilities. Depending on the specific application implemented, one or more analytes such as glucose, ketone, etc., may be monitored. SCA 304 and UDPD 200 are in communication with adapter 1701 and uses adapter 1801 to communicate with remote sensor device 1820. Remote sensor device 1820 obtains analyte measurement data taken from user 1825 and communicates the data to SCA 304 and UDPD 200 via adapter 1801. SCA 304 receives the measurement data and provides additional monitoring capabilities such as those described herein—e.g., displaying and/or audibly outputting the measurement reading, logging the measurement data, providing alarms, calculating medication dosages, communicating with drug administration devices, etc.

Turning back to FIG. 3, after installation on UDPD 200, test harness 310 is executed to determine whether SCA 304 operates properly on UDPD 200, as represented by reference circle number three. In some instances, test harness 310 and SCA 304 are configured such that test harness 310 is initiated before SCA 304 is freely operational.

The terms "freely operational" and "operating freely" are used herein to refer to the SCA operating such that the user is able to use the SCA as intended and free of any restrictions implemented by the test harness. It should be appreciated that one or more safety critical features of the SCA may be "intended" to be locked or disabled (e.g., by the manufacturer, physician, etc.) from the user, and the running of the SCA with the intentionally locked features is considered to be operating freely.

However, if the test harness restricts the use of the SCA, then the SCA is said to be prevented from operating freely. For example, in some instances, this may include disabling the SCA and preventing the SCA from being run on the UDPD. In some instances, this may include locking or disabling of one or more safety critical features of the SCA. In some instances, this may include permitting the SCA to run on the UDPD so that the user may still use non-safety critical features of the SCA but unable to use all safety critical features of the SCA. One or more checks on test harness 310 may be performed before SCA 304 is freely operational to provide a certain level of assurance that SCA 304 may operate properly on UDPD 200 before the user uses the safety critical features. Further, in some instances, one or more checks on test harness 310 may be performed during and/or after SCA is freely operational to provide a certain level of assurance that that SCA 304 continues to operate properly on UDPD 200.

It should be appreciated that the term "permitting" is used broadly herein and may include allowing, enabling, unlocking, etc., in some instances. Further, it should be appreciated that the term "preventing" is used broadly herein and may include restricting, disabling, locking, etc., in some instances.

In some aspects of the present disclosure, test harness 310 comprises one or more of the following checks: an installation check to determine if SCA 304 was installed properly on UDPD 200; a functional check to determine if SCA 304 functions properly on UDPD 200; a host integrity check to determine if the integrity of SCA 304 has been compromised; a coexistence check to determine if SCA 304 is incompatible with other programs on UDPD 200; an interoperability check to determine if SCA 304 interoperates properly on UDPD 200 with related programs; a power management check to determine if the power capabilities of UDPD 200 are sufficient to run SCA 304 safely with a certain level of assurance that the UDPD will not abruptly shutdown; and an environment check to determine a current environment of UDPD 200 at various times (e.g., when checks are initiated) and/or determine if a change in environment has occurred since a previous determination of a current environment (e.g., at a time associated with the last time the SCA was determined to operate properly on the UDPD). Furthermore, test harness 310 may execute one or more of these checks at various times—e.g., before SCA 304 is run, while SCA 304 is being run, at predetermined intervals, etc.—and in different combinations as desired.

In some aspects of the present disclosure, executing test harness 310 results in one or more checks being executed to determine whether SCA 304 is operating properly on UDPD 200 and control the operation of SCA 304 on UDPD 200 accordingly. For example, SCA 304 and test harness 310 may be configured such that SCA 304 is prevented from operating freely on UDPD when determined that SCA 304 is not operating properly on UDPD 200.

In some instances, test harness 310 may be run in the background of UDPD 200. SCA 304 and/or other software programs may, in some instances, be run in the foreground while test harness is run in the background on UDPD 200. Furthermore, it should be appreciated that, in some instances, the running of the test harness in the background may be transparent to the user.

In some instances, test harness 310 and SCA 304 are part of larger program module 302 (also referred to herein as "program 302"), as represented by dotted lines. For example, the entire program 302 is initially verified and validated, and subsequently installed on UDPD 200. Program 302 may be configured to initiate test harness 310 before allowing SCA 304 to operate freely. In this way, test harness 310 is initiated, in order to determine if SCA 304 may operate properly (e.g., installed and functioning properly) on UDPD 200, and thus control the operation of SCA 304 on UDPD 200 accordingly (e.g., permit or prevent SCA 304 from operating freely on UDPD 200).

In some instances, SCA 304 and test harness 310 are separate programs which may be initially verified and validated separately, and further may be installed on UDPD 200 at the same or different times. In such cases, SCA 304 is configured to execute test harness 310 at the appropriate times. For example, SCA 304 may include commands to initiate test harness 310 prior to SCA 304 being able to operate freely. In some instances, if SCA 304 is installed on UDPD 200 and test harness 310 is not, then SCA 304 is configured to prevent SCA 304 from operating freely.

In some instances, test harness 310 may be included within SCA 304. A new SCA 304 may be written to include a test harness 310, or an existing SCA 304 may be modified to include test harness 310. In such case, SCA 304 may be configured to initiate the test harness at the appropriate times. For example, SCA 304 may include commands to execute test harness 310 before SCA 304 is freely operational (e.g., before safety critical features are accessible to the user). In this way, a determination can be made as to the proper operation of SCA 304 on UDPD 200 before the user ever uses the safety critical features of SCA 304. Test harness 310 may also be implemented within SCA 304 such that it may be called upon one or more times or at various times as desired. It should be appreciated that SCA 304 and test harness 310 are shown separate in some figures herein for illustrative purposes, and that embodiments with test harness 310 included within SCA 304 are applicable as well.

Figure 4:
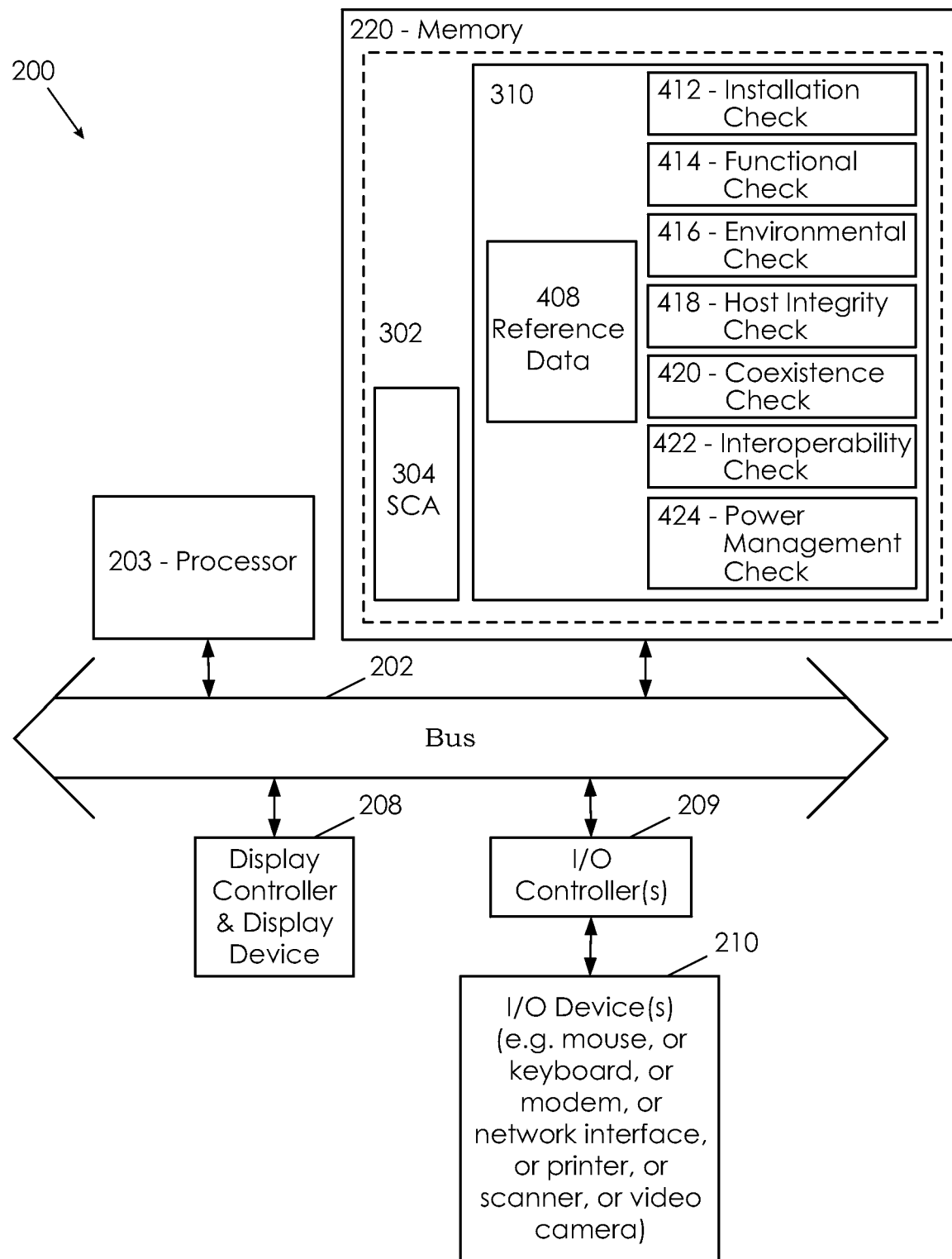
FIG. 4 illustrates a functional block diagram of SCA and test harness stored in memory of a UDPD, according some aspects of the present disclosure.

FIG. 4 illustrates a functional block diagram of SCA and test harness accessible to UDPD 200, according some aspects of the present disclosure. It should also be appreciated that although test harness 310 and SCA 304 have been shown in memory 220 of UDPD 200 in FIG. 4, either or both may be embodied as machine-executable instructions on a machine-readable medium which is not necessarily local to or part of UDPD 200, but at some point accessed by UDPD 200 in any suitable manner.

UDPD 200 is shown in FIG. 4 to include, as previously described, a system bus 202 which is coupled to processor 203, memory 220, display controller and display device 208, and peripheral devices such as I/O devices 210. Memory 220 is shown to include SCA 304 and test harness 310. Again, SCA 304 and test harness 310 may be part of a larger program 302. It should be appreciated that memory 220 refers generally to any volatile and/or non-volatile memory available to processor 203, and may include one or more memory components. Furthermore, either SCA 304 or test harness 310, or both, may be stored in one or more memory components, and further may be stored together or separate from one another in removable or non-removable memory. It should also be appreciated that in some instances SCA 304 and test harness 310 may be stored in non-volatile memory and loaded into volatile memory such as RAM for execution by processor 203.

In some aspects of the present disclosure, test harness 310 may comprise one or more hardware and/or software modules for performing the checks and processes described herein. The checks and processes described herein, may for example, be executed by processor 203 of UDPD 200. It should be understood that the operations described for the checks (including test routines and subroutines) and processes described herein are accordingly performed by the host UDPD. As shown in the exemplary embodiment of FIG. 4, test harness 310 includes modules for an installation check 412, functional check 414, environment check 416, host integrity check 418, coexistence check 420, interoperability check 422, and power management check 422. These checks are initiated to determine whether SCA 304 may operate properly on UDPD 200.

Test harness 300 may be configured to run one or more of checks at various times as desired to perform the functions associated with each check: an installation check to determine if SCA 304 was installed properly on UDPD 200; a functional check to determine if SCA 304 functions properly on UDPD 200; a host integrity check to determine if the integrity of SCA 304 has been compromised; a coexistence check to determine if SCA 304 is incompatible with other programs on UDPD 200; an interoperability check to determine if SCA 304 interoperates properly on UDPD 200 with related programs; a power management check to determine if the power capabilities of UDPD 200 are sufficient to run SCA 304 safely with a certain level of assurance that the UDPD will not abruptly shutdown; and an environment check to determine a current environment of UDPD 200 at various times (e.g., when checks are initiated) and/or determine if a change in environment has occurred since a previous determination of a current environment (e.g., at a time associated with the last time the SCA was determined to operate properly on the UDPD).

A determination that SCA 304 operates properly on UDPD 200 may require specific outcomes for each check that is implemented. For example, in some instances, a determination that SCA is operating properly on UDPD requires an installation check to indicate that SCA is installed properly and also requires a functional check to indicate that SCA is functioning properly on UDPD 200. In some instances, a determination that SCA is operating properly on UDPD requires only functional check to indicate that SCA is functioning properly on UDPD 200 (e.g., if a proper installation has already been determined). A determination that SCA 304 is not operating properly on UDPD 200 may result, for example, from either a determination that SCA is not installed properly or a determination that SCA is not functioning properly. It should be appreciated that additional checks (e.g. host integrity check, coexistence check, interoperability check, power management check, and/or other checks not necessarily discussed herein) may also be implemented, with their specific outcomes also required for a determination that SCA operates properly on UDPD.

The environment of the UDPD refers generally to various software and/or hardware components, or their configurations thereof, which are present on UDPD. For example, the environment check may identify various software programs, applications, drivers, hardware components, etc., that are currently on the UDPD, that have been installed and/or removed and/or modified, etc. In some embodiments, only the software environment may be taken into consideration. In some embodiments, the hardware environment may also be taken into consideration.

In some instances, the environment check is implemented to check to see if the environment of UDPD has changed, which may be a possible indicator that SCA no longer operates properly on UDPD. In such cases, one or more additional checks (e.g., functional check, host integrity check, coexistence check, interoperability check, power management check, etc.) may be executed to confirm that SCA is operating properly on UDPD in the new environment.

In some instances, as shown in FIG. 4, test harness also includes reference data 408. Reference data 408 includes data used by test harness 310 to determine whether SCA 304 is performing within predetermined parameters and requirements that are associated with a certain level of confidence that SCA 304 is operating properly on UDPD 200. For example, reference data 408 may include various test data to be used in the checks (e.g., predetermined input data or requests) as well as any data, results, timing values, etc., that are acceptable or expected to result from various checks to indicate proper operation of the UDPD. It should be understood that some parameters and requirements may encompass ranges and/or include tolerances which allow for some level of deviation.

Installation Check—In some aspects of the present disclosure, an installation check 412 may be executed to determine whether SCA 304 is installed properly on UDPD 200. Because an improperly installed SCA compromises any assurance that the SCA is going to operate properly on UDPD, a successful installation of SCA 304 may be required in order to determine that SCA 304 operates properly on the UDPD. Thus, in some instances, if SCA 304 failed to install properly on UDPD 200, then it may be determined that SCA 304 does not operate properly on UDPD 200 and SCA 304 may be prevented from operating freely on UDPD 200. If installation check indicates that SCA 304 installed properly on UDPD 200, however, SCA 304 may still not necessarily operate properly on UDPD and additional checks may be required before determining that the SCA operates properly on the UDPD.

In some instances, images of installed components of SCA 304 (also referred to herein as "installed SCA components") may be used to determine whether SCA 304 is installed properly on UDPD 200. For example, an installation package for SCA 304 may include a plurality of files that are loaded onto UDPD 200 in addition to a primary executable file. Installation check 412 may view each of these files as an installed SCA component and compare images of each installed SCA component against reference data 408 corresponding to data that is expected for a proper installation (also referred to herein as "reference installation data" to distinguish it from other data that may be within reference data 408). For instance, in some instances, an image of an installed SCA component may include data about the installed SCA component, such as filename, version number, error detection and/or error correction data (e.g., cyclic redundancy check (CRC) value, error correcting code (ECC), checksum, etc.), etc. Installation check 412 compares the data for each installed SCA component against expected data associated with a proper installation (e.g., as defined by the reference installation data) to determine whether a proper installation has occurred. For example, a filename, CRC value, and/or version number associated with the installed SCA component may be compared with corresponding expected filename, CRC value, and/or version number in the reference installation data.

If, for example, the image of one or more installed SCA components does not match the reference installation data, then installation check 412 indicates that SCA 304 failed to install properly on UDPD 200, which indicates that SCA 304 does not operate properly on UDPD 200. SCA 304 may then be prevented from operating freely on UDPD 200. In some instances, a failure to install properly may be reported (e.g., logged and/or communicated to the user of UDPD 200). In some instances, a report of the failure may be sent to a remote device—e.g., via the internet.

If, for example, the image of each installed SCA component matches the reference installation data, then the installation check indicates that SCA 304 installed properly on UDPD 200 and one or more other checks (e.g., functional check, host integrity check, coexistence check, interoperability check, power management check, etc.) may be executed if required. The term "match" is used broadly herein to indicate falling within predetermined parameters and requirements (e.g., as defined by the reference data). A resulting match for the installation check thus represents a certain level of confidence that SCA 304 installed properly on UDPD 200. In some instances, the predetermined parameters and requirements require an "exact" match. However, it should be appreciated that, in some instances, parameters and requirements may encompass ranges and/or tolerances which allow for some deviation from an "exact match" requirement. Accordingly, the term "non-match" is used broadly herein to indicate not falling within the predetermined parameters and requirements (e.g., as defined by reference data). A resulting non-match for the installation check thus represents a certain level of confidence that SCA 304 did not install properly on UDPD 200.

Functional Check—In some aspects of the present disclosure, a functional check 414 may be executed to determine whether SCA 304 functions properly on UDPD 200. For example, functional check 414 may check whether SCA 304 performs computations (e.g., calculations, measurements, etc.) accurately on UDPD 200; whether SCA 304 displays data properly on a display of UDPD 200; and/or whether SCA 304 communicates properly via UDPD with an external device; and/or whether SCA 304 performs these and/or other safety critical activities in a proper amount of time.

A delay in performing an activity may have detrimental consequences and may indicate improper operating of SCA 304 on UDPD 200. For example, a significant delay in providing a computation for a glucose measurement may be sufficient to determine that SCA 304 is not operating properly on UDPD 200. Further, it should be appreciated that in some instances, performing an activity such as a computation too quickly may be indicative of improper functioning as well. Functional check 414 may also, for example, check whether data for SCA 304 is displayed properly on a display of UDPD 200; and/or whether SCA 304 may communicate properly between UDPD 200 and an external device.

If, for example, it is determined that SCA 304 does not function properly, then functional check 414 indicates that SCA 304 does not operate properly on UDPD 200. SCA 304 may then be prevented from operating freely on UDPD 200. If, for example, it is determined that SCA 304 functions properly, then other checks may also be initiated as required (or if no other checks are required to be executed, then SCA may be permitted to operate freely).

Environment Check—In some aspects of the present disclosure, an environment check 416 may be executed to determine a current environment of UDPD 200. Further, in some instances, environment check 416 may be executed to determine whether the current environment has changed since the last determination that SCA 304 is operating properly on UDPD 200. Changes to the environment of the UDPD may affect the proper operation of SCA 304 on UDPD 200. Thus, in some instances, the environment check may include identifying the current environment and comparing it to a previously stored 'current environment' that was associated with the last determination that SCA 304 is operating properly on UDPD 200.

For example, test harness 310 may initiate environment check 416 to obtain a current environment of UDPD 200 when it is determined that SCA is operating properly and permitted to operate freely on UDPD 200. In this way, test harness 310 may later initiate environment check 416 to determine if the 'current environment' of UDPD 200 has changed since this determination that SCA is operating properly. It should be appreciated that the current environment may be identified and recorded at various times associated with the performing of the checks—e.g., before the check is initiated, while the check is initiated, or after the check has provided an outcome.

If it is determined that the environment of UDPD 200 changes, then SCA 304 may potentially operate improperly on UDPD 200. Test harness 310 may then, for example, initiate a functional check (or any additional checks if implemented as well) to be executed. In some instances, SCA 304 may be permitted to continue to operate freely while the functional check is being performed. In some instances, SCA 304 may be prevented from operating freely while the functional check is being performed.

If it is determined that environment of UDPD 200 does not change, then a certain level of confidence is achieved that SCA 304 is still operating properly on UDPD 200. SCA 304 may, for example, be permitted to continue operating freely if the environment of UDPD 200 does not change. It should be appreciated that one or more checks may be initiated if desired, despite the determination that the environment has not changed.

Environment check may be initiated at various times as desired—e.g., at predetermined times and/or time intervals (while SCA is running and/or not running); upon occurrences of certain events (e.g., when SCA 304 is run, when SCA 304 is closed, when the UDPD is powered, etc.). In some instances, additional checks such as functional check 414 may be initiated independent of the environment check 416 and may also be initiated at various times (e.g., at predetermined times and/or upon occurrences of certain events).

Host Integrity Check—In some aspects of the present disclosure, a host integrity check may be executed to determine if the integrity of SCA 304 has been corrupted. A corrupted SCA 304 compromises any assurance that SCA 304 operates properly on UDPD 200. In some instances when a host integrity check is implemented, a determination that SCA 304 operates properly on UDPD 200 requires at least a determination that SCA 304 is not corrupted. If SCA 304 is corrupted, it may be determined that SCA 304 does not operate properly on UDPD 200 and SCA 304 may be prevented from operating freely on UDPD 200. If SCA 304 is determined to be uncorrupted, then it may be determined that SCA 304 operates properly and permitted to operate freely, as long as any other required checks performed, or to be performed, are successfully passed as well.

Coexistence Check—UDPD 200 typically hosts additional programs loaded on the device in addition to SCA 304. Furthermore, programs may typically be added to and/or deleted from UDPD 200 at different times. Some of the programs on UDPD 200 may not work together with SCA 304 but may share resources with SCA 304, referred to herein as "nonrelated" programs. SCA 304 and one or more non-related programs may, for example, access one or more persistent area of data. For instance, both may track data & time, read and/or write data to the same memory device, etc. Moreover, both SCA 304 and the non-related program(s) may access the same components—e.g., wireless chip, display, audio components, etc.

For some of the nonrelated programs, SCA 304 may not be affected, or affected in ways that do not threaten the safety critical nature of SCA 304, when coexisting on UDPD 200 with SCA 304. However, some programs may not be able to coexist on UDPD 200 with SCA 304 without compromising a safety critical aspect of SCA 304, or operation thereof, on UDPD 200. For example, a nonrelated program that is running may prevent or significantly delay SCA 304 from access to a safety critical function such as displaying a test result, sounding an alarm, accessing wireless communication, etc. If these functions are safety critical features, the coexistence of the two programs on UDPD 200 may pose safety critical issues that potentially prevent SCA 304 from operating properly on UDPD 200 and SCA 304 may be prevented from operating freely.

In some instances, the SCA 304 may have priority access to resources in certain circumstances. For example if an expected time for receipt of data from another device (e.g., a medical device such as an analyte monitoring device, drug administration device, etc.) is exceeded by a predetermined amount of time, SCA 304 may be give priority access to information outputs for the UDPD 200 to activate an alarm, for example. As part of this priority access, an automatic save state may be initiated, for example, for other modules operating on the UDPD 200. Additionally, SCA 304 may be give priority access to communication ports on the UDPD 200—e.g., to communicate the alarm to a third party such as parent, friend, physician, etc. The SCA 304 may, for example, have priority access to wireless communication devices, memory, processors, and/or any other shared resource that may be prioritized.

In some aspects of the present disclosure, a coexistence check may be executed to determine if SCA 304 is incompatible with non-related programs on UDPD 200. The term 'incompatible" is used broadly herein to mean that SCA 304 and other program(s) cannot coexist on UDPD 200 without compromising the safety critical aspects of SCA 304, or operation thereof, on UDPD 200.

In some instances, when a coexistence check is implemented, a determination that SCA 304 operates properly on UDPD 200 requires at least a determination that SCA 304 is not incompatible with any non-related program. If SCA 304 is incompatible with one or more nonrelated programs, then SCA 304 may be prevented from operating freely on UDPD 200. If SCA 304 is not incompatible with any nonrelated programs, then it may be determined that SCA 304 operates properly and thus permitted to operate freely on UDPD 200, as long as any other required checks performed, or to be performed, are successfully passed as well.

Interoperability Check—One or more programs may interoperate with SCA 304 to provide functionality and capabilities to SCA 304, referred to herein as related programs. In some aspects of the present disclosure, an interoperability check may be executed to determine if SCA 304 interoperates properly on UDPD 200 with related programs. Interoperability problems may compromise any assurance that SCA 304 is going to operate properly on UDPD 200. In some instances, a determination that SCA 304 operates properly on the UDPD requires at least a determination that SCA 304 interoperates properly with related programs. If SCA 304 does not interoperate properly with related programs, then it may be determined that SCA 304 does not operate properly and SCA 304 may be prevented from operating freely on UDPD 200. If SCA 304 is determined to interoperate properly, then it may be determined that SCA 304 operates properly on the UDPD and thus permitted to operate freely, as long as any other required checks performed, or to be performed, are successfully passed as well.

Power Management Check—Some UDPDs may be battery powered and not necessarily plugged into an AC power outlet. Thus, the life of UDPD 200 is volatile in the sense that UDPD 200 could run out of power and shut down during operation of SCA 304. Battery power may be dependent upon a number of factors—e.g., type and size of battery used, the type and amount of activity performed by UDPD 200, etc. Unexpected or early power loss could compromise the safety critical nature of a SCA 304.

In some aspects of the present disclosure, a power management check may be executed to determine if the power capabilities of UDPD 200 are sufficient to run SCA 304 safely with a certain level of assurance that the UDPD will not abruptly shutdown. For instances, the power capabilities may be determined and compared to a minimum threshold amount required to operate SCA 304 safely with minimal risk of an abrupt shutdown. In some instances, a determination that SCA 304 operates properly requires at least that the UDPD have sufficient power capabilities to operate safely with minimal risk of shutdown. If UDPD 200 has sufficient power capability, then SCA 304 may be determined to operate properly on UDPD 200 and permitted to operate freely on UDPD 200, as long as any other required checks performed, or required to be performed, are successfully passed as well. If UDPD 200 does not have sufficient power capability, then SCA 304 may be prevented from operating freely.

Figure 5:
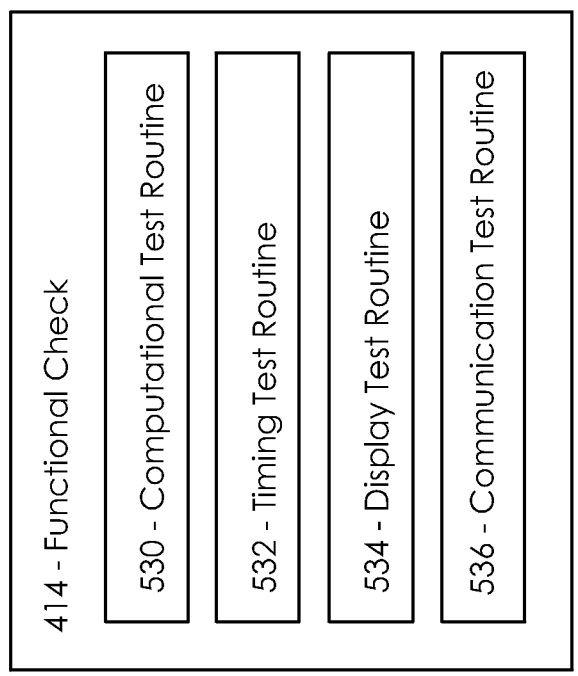
FIG. 5 illustrates a block diagram of a functional check comprising one or more test routines, according to some aspects of the present disclosure.

In some embodiments, a check may include one or more test routines to be initiated. FIG. 5 illustrates a block diagram of a functional check comprising one or more test routines, according to some aspects of the present disclosure. As shown, functional check 414 includes computational test routines 530, timing test routines 532, display test routines 534, and communication test routines 536.

Computational test routines 530 determine whether SCA 304 is performing computations accurately on UDPD 200—e.g., within predetermined parameters and requirements that represent a certain level of confidence that SCA 304 is computing accurately on UDPD 200. The predetermined parameters and requirements may be defined, for example, by reference data 408 (also referred to herein as "reference computational data" to distinguish it from other data that may be within reference data 408).

Specific computations may vary depending on the specific safety critical features implemented within SCA 304. Computations may include, for example, various calculations, measurements, extrapolations, etc., for a wide variety of applications, such as medical applications and other SCAs. For example, computations for analyte monitoring applications may include, but are not limited to, computing analyte (e.g., glucose) measurements, calculating medicine dosages and/or administration times (e.g., insulin dosages from received glucose measurements), executing various other therapy-related algorithms (e.g., trending calculations, various alert determinations, etc.), and/or other safety critical computations that are applicable to analyte monitoring.

In some instances, execution of computational test routines 530 may initiate specific computations to be performed by SCA 304 using predetermined input data (e.g., as defined by reference data 408, referred to herein as "reference computational input" to distinguish it from other data that may be within reference data 408). Accordingly, reference computational data include the expected or acceptable results for these computations using the reference computational input. The actual result of the computation and the reference computational data may be compared to determine if the computations are performed accurately on UDPD 200.

Reference computational input may simulate, for example, safety critical input data provided to SCA 304 and UDPD 200 while SCA 304 is operating freely. For example, when operating freely, SCA 304 and UDPD 200 may be configured to receive data from one or more external devices (e.g., analyte measurements, such as glucose measurements, from external analyte monitoring devices, such as a glucose monitoring devices) and then perform various computations on the received data. Computational test routines 530 initiate such computations by SCA 304 and UDPD 200 using reference computational input which simulates such received data (e.g., analyte measurements from an external device). The results of the computations may then be compared against the corresponding reference computational data to determine if SCA 304 is computing accurately on UDPD 200.

If, for example, it is determined that SCA 304 does not perform the computations accurately (e.g., results of the computation do not match the reference computational data), then computation test routines 530 indicates that SCA 304 is not functioning properly on UDPD 200, which further indicates that SCA 304 is not operating properly on UDPD 200. SCA 304 may then be prevented from operating freely on UDPD 200.

In some instances, a determination that SCA 304 functions properly on UDPD 200 requires at least a determination that SCA 304 performs computations accurately (e.g., a match between the result of the computation and the reference computational data). It should be appreciated that although a condition is required for SCA to function properly, that does not necessary mean that SCA functions properly if that condition is met—other conditions may also be required to be met. For example, in some instances, in order for SCA to function properly it may be required that SCA 304 performs computations accurately (e.g., results of the computation match the reference computational data), as well as be required that SCA performs computations in a timely manner. Thus, the occurrence of one condition alone does not necessarily mean SCA functions properly. If, for example, it is determined that SCA 304 performs computations accurately (e.g., results of the computation match the reference computational data), then other checks and/or test routines may be initiated (or if no other checks and/or test routines are required to be executed, then SCA may be permitted to operate freely).

Timing test routines 532 determine whether SCA 304 performs activities (e.g., computations, communications, etc.) on UDPD 200 in a timely manner—e.g., within times falling within predetermined parameters and requirements that represent a certain level of confidence that SCA 304 is performing the activities in a timely manner on UDPD 200. The predetermined parameters and requirements may be defined, for example, by reference data 408 (also referred to herein as "reference timing data" to distinguish it from other data that may be within reference data 408) Activities may include any variety of activities implemented by SCA 304—e.g., safety critical computations such as described above, displaying of various results on a display of UDPD 200, communications to external devices, executing of checks and test routines, any combination thereof, etc.

For example, timing test routines 532 may determine the time it takes for SCA 304 to perform computations initiated by computational test routines 530. In some instances, for example, time stamps or logs of particular events or duration of events may be recorded. For example, various times associated with the execution of computational test routines 530 may be logged or recorded—e.g., the time when reference computational input is provided to SCA 304, and the time when corresponding results are provided by SCA 304 (the difference of the two times representing the time it took SCA 304 to perform the computation on UDPD 200). In some instances, the additional time it takes to display the information is taken into account. It should be appreciated that a timer may also be implemented or any other suitable method of tracking time.

The timing results may then be compared against corresponding reference timing data to determine whether SCA 304 is performing activities (e.g., computations, communications, etc.) on UDPD 200 in a timely manner. Again, it should also be appreciated that, in some instances, the performance of an activity in too short of a time period may be indicative of SCA 304 not performing in a timely manner on the UDPD.

If, for example, it is determined that SCA 304 does not perform activities in a timely manner (e.g., the time to perform the activity does not match the reference timing data) on UDPD 200, then timing test routines 532 indicates that SCA 304 is not functioning properly on UDPD 200, which further indicates that SCA 304 is not operating properly on UDPD 200. SCA 304 may then be prevented from operating freely on UDPD 200.

In some instances, a determination that SCA 304 functions properly on UDPD 200 requires at least that SCA 304 perform activities in a timely manner (e.g., a match between the time to perform activities and the reference timing data). For example, if it is determined that SCA 304 performs activities in a timely manner (e.g., the time to perform the activity matches the reference timing data) on UDPD 200, then other checks and/or test routines may be initiated (or if no other checks and/or test routines are required to be performed, then SCA may be permitted to operate freely).

Display test routines 534 determine whether data for SCA 304 is properly displayed on UDPD 200—e.g., within predetermined parameters and requirements that represent a certain level of confidence that SCA 304 is displaying data properly on UDPD 200. The predetermined parameters and requirements may be defined, for example, by reference data 408 (also referred to herein as "reference display data" to distinguish it from other data that may be within reference data 408). In some instances, reference display data corresponds to an expected result of a computational test routine that is to be displayed on the display of UDPD 200.

Display test routines 534 may, for example, initiate specific predetermined images defined by reference data 408 (referred to herein as "reference display inputs" to distinguish it from other data that may be within reference data 408) to be displayed on a display of UDPD 200. Accordingly, reference display data may include the expected output image corresponding to the reference display inputs. The actual image displayed and the reference display data may then be compared to determine if data is being displayed properly on UDPD 200 (e.g., to determine if the actual image displayed matches the reference display data).

It should be understood that the term images is used broadly herein to include any form of data to be displayed on the display (e.g., pixel patterns, image files (e.g., JPEG, TIFF, GIF, BMP, etc.), text, numerals, etc. In some instances, a display pattern may be used. Furthermore, in some instances, display patterns may also be used to test various display diagnostics, such as timing/scan rates, smear, brightness, contrast, etc.

The actual image displayed on UDPD 200 may be determined in any of a variety of ways. In some instances, a screen capture may be taken. For example, display test routines 534 may include a print screen function call to initiate a screen capture for the image displayed on the display of UDPD 200). The actual image displayed on UDPD 200 may then be compared to the reference display data to determine if data is being properly displayed on UDPD 200. It should be appreciated that the print screen function does not require the UDPD to be connected to a printer, but rather illustrates that the display test routines 534 may "read" the display, which is normally a write only device.

It should also be appreciated that various comparison algorithms may be implemented to compare the actual image displayed on UDPD 200 with the reference display data. For example, in some instances, comparison algorithm may convert the actual image displayed to a representative value or expression. In such case, for example, the reference display data may be an expected representative value or expression of the reference display inputs. Thus, the two values or expression may be compared to determine if a match or non-match occurs. In some instances, the comparison algorithm may compare the images themselves, in which case the reference display data would be equivalent to the reference display inputs. It should be appreciated that any variety of methods of comparing may be implemented.

In some instances, the actual image displayed on UDPD 200 may be determined by receiving user input that identifies the actual image displayed on the display of UDPD 200. The user may be prompted, for example, to confirm the accuracy of the display (e.g., to enter the numeral, text, symbol, or phrase that is displayed; or to provide any other form of confirmation response to information displayed on the display; etc.). In such instances, for example, user confirmation may function as the actual image displayed, and thus compared to reference display data that indicates what is expected to be displayed. In this way, it may be determined whether images are displayed on the UDPD properly.

For example, a request for user verification may be initiated to determine whether data is accurately displayed on UDPD 200. For instance, a verification inquiry may be conveyed (visually, audibly, etc.) to the user, prompting the user to input what is displayed on the display of the UDPD (e.g., an alphanumeric code, numeric code, symbols, text, phrases, etc.). The actual image displayed on the display may be determined by initiating an image (e.g., the code) to be displayed on the display of UDPD 200 and receiving user input identifying what is displayed. The actual image displayed identified by the user input may then be compared with reference display data to determine if the correct image is displayed.

Furthermore, the level of assurance that the user input accurately identifies the actual image displayed may vary based on the type of verification inquiry implemented. For example, a basic level of assurance can be achieved by having the user provide yes or no feedback. For example, the verification inquiry may ask if the user sees a specific image (e.g., "Do you see a car on the display?"). It should be appreciate that the image may be any variety of pictures, symbols, words, phrases, numbers, etc. The user may then respond to the inquiry by inputting the appropriate answer on the UDPD (e.g., typing "yes" or "no", touching the "yes" or "no" button on the touch screen, etc.). The user input identifying if the image is a car or not is received and compared with reference display data (e.g., a response of "yes" indicating that the image is properly displayed on the display; a response of "no" indicating that the image is not properly displayed on the display).

Another level of assurance can be achieved by using a verification inquiry that has the user respond to a multiple choice question. The greater the number of answer choices available reduces the chance of the user guessing and providing a false positive. For example, the verification inquiry may ask, "Do you see a car, tree, or the number 12 on the display?" The user may then respond to the verification inquiry by selecting or entering the appropriate answer. The user input identifying the actual image displayed on the display is then compared with reference display data that identifies what was expected to be displayed on the display.

Another level of assurance can be achieved by using a verification inquiry that has the user respond to an open question or command. For example, verification inquiry may ask, "What do you see?"; "Enter the text, code, symbol, etc., that you see on the display; etc. The user may then respond to the verification inquiry by entering the appropriate answer (e.g., by typing in what they see; entering the code, symbol, etc., displayed; etc.). The user input identifying the actual image displayed on the display is then compared with reference display data that identifies what was expected to be displayed on the display.

If, for example, it is determined that UDPD 200 does not display reference display inputs properly (e.g., the actual image displayed does not match the reference display data), then display test routines 534 indicates that SCA 304 is not functioning properly on UDPD 200, which further indicates that SCA 304 is not operating properly on UDPD 200. SCA 304 may then be prevented from operating freely on UDPD 200.

In some instances, a determination that SCA 304 functions properly on UDPD 200 requires at least that UDPD 200 displays reference display inputs properly. For example, if it is determined that UDPD 200 does display reference display inputs properly (e.g., the actual image displayed matches the reference display data), then other checks and/or test routines may be executed as desired (or if no other checks and/or test routines are required to be executed, then SCA may be permitted to operate freely).

In some embodiments, SCA 304 and UDPD 200 may be configured to communicate with an external device via a communication link (e.g., a wired or wireless communication link). Communication test routines 536 may be initiated to determine whether SCA 304 communicates properly on UDPD 200 with the external device. For instance, communication test routines 536 may determine whether SCA 304 may properly establish a communication link between UDPD 200 and the external device, whether SCA 304 may communicate (e.g., send and/or receive data) accurately, etc. The communications may also be required to be performed in a timely manner over the communication link for SCA 304 to be communicating properly with an external device via a communication link with UDPD. The communication test routines 536 may apply to unidirectional and/or bidirectional testing.

SCA 304 may communicate with external devices for various purposes depending on the specific SCA implemented. Looking ahead to FIG. 7, FIG. 7 illustrates a block diagram of a UDPD communicating with various external devices via communication links, according to some aspects of the present disclosure.

Figure 7:
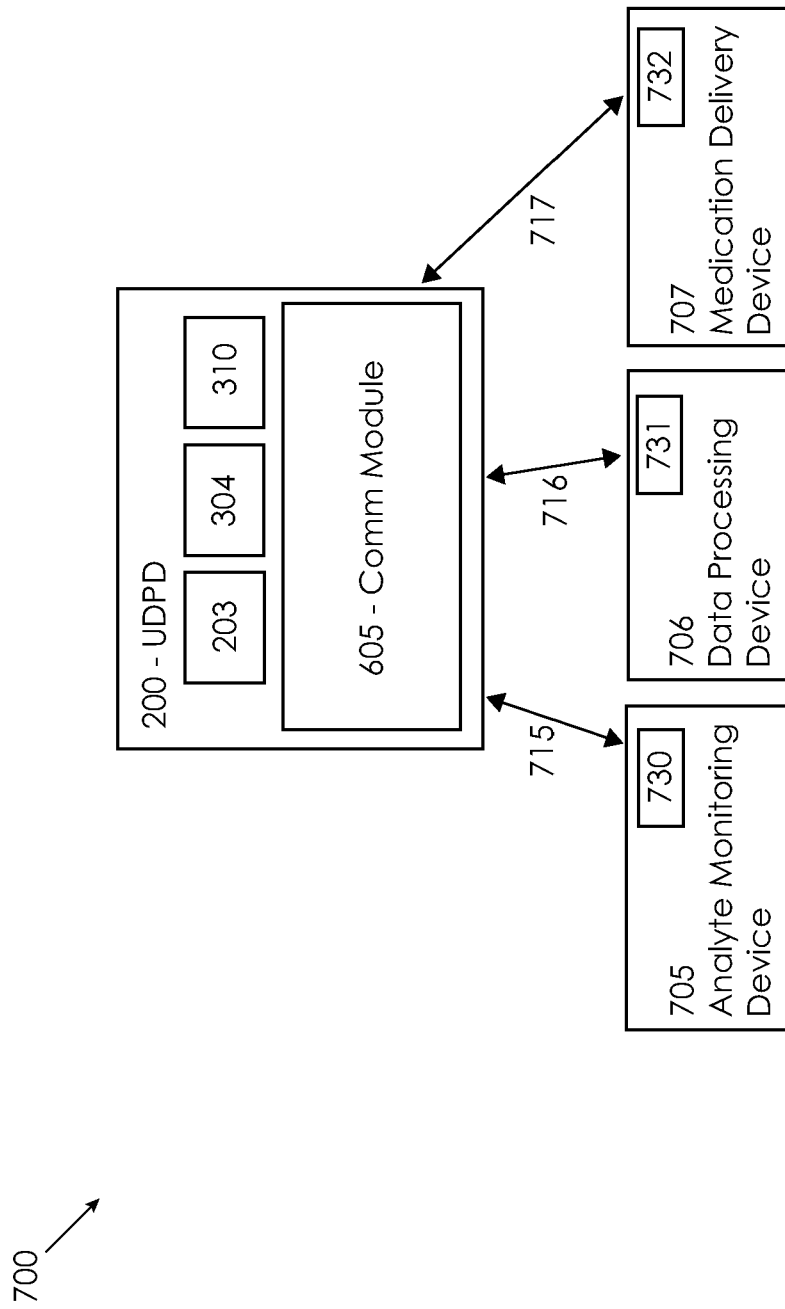
FIG. 7 illustrates a block diagram of a UDPD communicating with various external devices via communication links, according to some aspects of the present disclosure.

As shown in FIG. 7, system 700 comprises UDPD 200 communicating with an analyte monitoring device 705 via communication link 715; data processing device 706 via communication link 716, and medication delivery device 707 via communication link 717. UDPD 200 includes communication module 605 which forms communication links 715-717 with communication modules 730-732 of external devices 705-707, respectively. Communication module 605 and communication modules 730-732 may include, for example, appropriate transmitters, receivers, and/or transceivers. It should be appreciated that communication links 715-717 may be implemented with wired (e.g., USB, Ethernet, or any other suitable wired technology) or wireless technologies (e.g., Bluetooth, infrared, radio frequency identification (RFID), or any other suitable wireless technology). While communication module 605 is represented by one block, it should be appreciated that communication module 605 may comprise one or more communication modules of one or more communication technologies. For example, communication module 605 may include a Bluetooth module to communicate with one external device over Bluetooth and another infrared module to communicate with another external device over infrared. It should also be appreciated that UDPD 200 may be configured to communicate with one or more of the devices shown, or with another external device not shown.

UDPD 200 further includes processor 203 which executes various sets of instructions for SCA 304 and test harness 310, and further controls the operation of communication module 605. In some embodiments, UDPD 200 is a mobile phone, such as an iPhone® or Blackberry®, with SCA 304 and test harness 310 installed thereon. While a mobile phone is used to describe this particular embodiment, it should be appreciated that any UDPD may apply.

Analyte monitoring device 705 may be, for example, a glucose monitoring device such as a glucose meter. In some instances, analyte monitoring device 705 may be a continuous glucose monitoring (CGM) device and/or glucose on demand (GoD) device. For example, a CGM device and/or GoD device may comprise an implanted sensor that allows glucose measurement data to be taken from a patient and then transmitted to UDPD 200 via a wireless communication, such as Bluetooth, for use by SCA 304. Additional information for implanted sensors may be found in U.S. patent application entitled "Compact On Body Physiological Monitoring Devices And Methods Thereof", which is assigned to the assignee of the present application, Abbott Diabetes Care Inc., and the entirety of which is incorporated herein by reference for all purposes.

Medication delivery device 707 may be, for example, an insulin pump used to deliver insulin dosages based on received dosage calculation from SCA 304 on UDPD 200. UDPD 200 may receive glucose measurements from device 709, for example, and calculate the recommended insulin dosages based on the glucose measurements and then transmit the recommended dosages to medication delivery device 707.

Data processing device 706 may be, for example, any type of computer device, such as personal computers (e.g., desktop, notebook, etc.), mobile phones (e.g., iPhone®, Blackberry®, etc.), personal digital assistants (PDAs), etc. UDPD 200 may communicate with data processing device 706 for various purposes—e.g., transmitting and/or receiving test results, logging data, using network capabilities of data processing device 706, etc.

If, for example, it is determined that SCA 304 does not communicate properly on UDPD 200 with the external device, then communication test routines 536 indicate that SCA 304 does not function properly on UDPD 200, which further indicates that SCA 304 does not operate properly on UDPD 200. SCA 304 may then be prevented from operating freely on UDPD 200.

In some instances, a determination that SCA 304 functions properly on UDPD 200 requires that SCA 304 communicates properly on UDPD 200 with the external device. For example, if it is determined that SCA 304 communicates properly on UDPD 200 with the external device, then other checks and/or test routines may be initiated as required (or if no other checks are required to be executed, then SCA may be permitted to operate freely).

Figure 6:
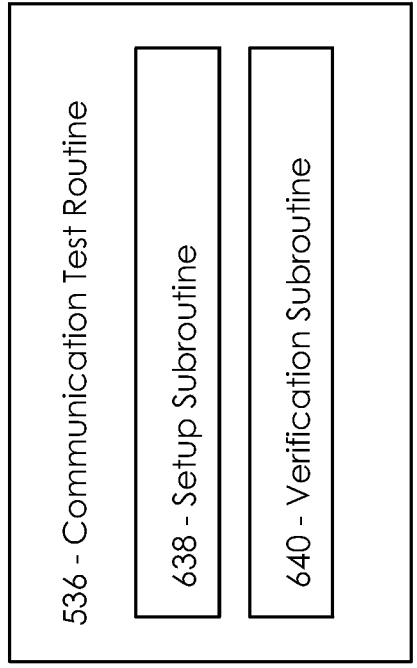
FIG. 6 illustrates a block diagram of a communication test routine comprising one or more subroutines, according to some aspects of the present disclosure.

In some embodiments, test routines may include one or more subroutines to be initiated. The terms "subroutines" and "test routines" are used herein to simply distinguish hierarchy between the two in order to facilitate understanding of the concepts presented herein. FIG. 6 illustrates a block diagram of a communication test routine comprising one or more subroutines, according to some aspects of the present disclosure. As shown, communication test routines 536 include communication setup subroutines 638 and communication verification subroutines 640.

Setup subroutines 638 are initiated to determine whether SCA 304 may properly establish a communication link between UDPD 200 and an external device. Execution of setup subroutines 538 may initiate SCA 304 to establish a communication link between UDPD 200 and an external device. For example, SCA 304 may attempt to establish a communication link between UDPD 200 and an analyte monitoring device and/or medication delivery device. For example, the SCA on the UDPD may communicate with an insulin pump to provide dosage data, for example. It should be appreciated that any variety of methods may be implemented to determine if the communication link is established properly—e.g., using a handshake process, by detecting a beacon signal from the external device, etc.).

If, for example, it is determined that SCA 304 may not properly establish a communication link between UDPD 200 and an external device, then communication setup subroutines 638 indicates that SCA 304 does not communicate properly between UDPD 200 and the external device, which indicates that SCA 304 does not function properly on UDPD 200, which further indicates that SCA 304 does not operate properly on UDPD 200. SCA 304 may then be prevented from operating freely on UDPD 200.

In some instances, a determination that SCA 304 communicates properly on UDPD 200 requires a determination that SCA 304 may properly establish a communication link between UDPD 200 and the external device. For example, if it is determined that SCA 304 may properly establish a communication link between UDPD 200 and an external device, then other checks and/or test routines and/or subroutines may be initiated as required (or if no other checks and/or test routines and/or subroutines are required to be executed, then SCA may be permitted to operate freely).

Verification subroutines 640 are executed to determine whether SCA 304 communicates (e.g., send and/or receive data) accurately over the communication link between UDPD 200 and the external device—e.g., within predetermined parameters and requirements that represent a certain level of confidence that SCA 304 is communicating accurately between UDPD 200 and the external device. The predetermined parameters and requirements may be defined by reference data 408 (also referred to herein as "reference communication data" to distinguish it from other data that may be within reference data 408).

In some instances, execution of verification subroutines 640 may initiate specific communications to be performed between UDPD 200 and the external device using reference data provided by the verification subroutines (referred to herein as "reference communication inputs" to distinguish it from other data that may be within reference data 408). Reference communication inputs may be any variety of data—e.g., a test signal, a request for data, etc. In some instances, execution of verification subroutines 640 may initiate SCA 304 to send out data to the external device to be "echoed" back. The echoed data received may then be compared to the data sent out to determine if the data was sent and returned without any data compromised or corrupted. For example, if SCA 304 is a glucose monitoring application that is designed to wireless communicate with an insulin pump, execution of the verifications subroutines 640 may initiate data to be sent to the insulin pump to be echoed back. The received echoed data may then be compared to the data transmitted. As another example, in some instances, execution of verification subroutines 640 may initiate SCA 304 to request data from the external device. For example, if SCA 304 is a glucose monitoring application that is designed to communicate via Bluetooth with a continuous glucose monitoring device, then execution of the verification subroutines 640 may initiate SCA 304 to request data from the continuous glucose monitoring device over the Bluetooth link.

Accordingly, reference communication data may include expected or acceptable results for the communications initiated using the reference communication inputs (e.g., test signal, request for data, etc.). The reference communication data may include, for example, the expected test signal (e.g., expected "echoed" signal), expected confirmation signals in response to transmitted test signals; expected data in response to requests for data; expected values; expected type of data (e.g., text, numerals, picture/movie file, etc.); expected communication protocol used, any combination thereof, etc.

The actual results of the communications (e.g., the test signal received, the response to the test signal, the confirmation signal received, the data received in response to a request for data, the expected value, the type of data received, the communication protocol used, any combination thereof, etc.) is compared with the reference communication data to determine if they match or do not match. Verification subroutines 640 may then determine whether SCA 304 communicates accurately over the communication link between UDPD 200 and the external device.

If, for example, it is determined that SCA 304 does not communicate accurately over the communication link between UDPD 200 and the external device, then verification subroutines 640 indicates that SCA 304 does not communicate properly between UDPD 200 and the external device, which indicates that SCA 304 does not function properly on UDPD 200, which further indicates that SCA 304 does not operate properly on UDPD 200. SCA 304 may then be prevented from operating freely on UDPD 200.

In some instances, a determination that SCA 304 communicates properly on UDPD 200 requires a determination that SCA 304 communicates accurately over the communication link between UDPD 200 and the external device. For example, if it is determined that SCA 304 does communicate accurately over the communication link between UDPD 200 and the external device, then other checks and/or test routines and/or subroutines may be initiated as required (or if no other checks and/or test routines and/or subroutines are required to be executed, then SCA may be permitted to operate freely).

Timing test routines 532 may be executed to determine whether SCA 304 performs communications on UDPD 200 with an external device in a timely manner—e.g., within times falling within "reference timing data" that represent a certain level of confidence that SCA 304 is communicating in a timely manner on UDPD 200 with an external device.

For example, timing test routines 532 may determine the time it takes for SCA 304 to properly establish a communication link between UDPD 200 and an external device initiated by setup subroutines 638, and/or to perform communications initiated by verification subroutines 640. Again, various times associated with the communication test routines 536 may be logged or recorded to determine whether SCA 304 is performing communications in a timely manner. In some instances, timing information may be included with the reference communication inputs (e.g., with the test signal, data request, etc.) sent to the external device, and/or timing information provided in the data sent by the external device. In this way, the timing of each one way communication may be determined.

Furthermore, it should be appreciated that communication test routines may include a timing subroutine that fulfills the same functions as the timing test routines 532 with respect to communication times.

If, for example, it is determined that SCA 304 does not perform the communication (and/or does not establish a communication link) in a timely manner (e.g., the time does not match the reference timing data) on UDPD 200, then timing test routines 532 indicates that SCA 304 does not communicate properly on UDPD 200, which indicates that SCA 304 does not function properly on UDPD 200, which further indicates that SCA 304 is not operating properly on UDPD 200. SCA 304 may then be prevented from operating freely on UDPD 200.

In some instances, a determination that SCA 304 communicates properly on UDPD 200 requires that SCA 304 performs the communication and/or establishes a communication link in a timely manner (e.g., the times match the reference timing data). For example, if it is determined that SCA 304 performs the communication and/or establishes a communication link in a timely manner on UDPD 200, then other checks and/or test routines may be initiated if required (or if no other checks and/or test routines are required to be executed, then SCA may be permitted to operate freely).

In some aspects of the present disclosure, a loopback hardware module may be implemented to perform various loopback tests on the UDPD. The loopback testing may determine, for example, if other components such as communication ports on the UDPD are operating properly. For instance, the loopback module may be a physical hardware device that couples to a communication port on the UDPD and receives a test communication from the UDPD and returns the test signal. It should be appreciated communication port is used broadly herein to encompass any type of communication receptacle or plug using any type of communication technology—e.g., any of the USB family, including Mini-USB and Micro-USB; Firewire; Ethernet; etc.

For example, test harness may comprise a test routine that may be executed to send a test signal to a communication port of the UDPD that has the loopback module attached. The loopback module receives the test signal and "echoes" it back via the same communication port. In some instances, the loopback module may be coupled to more than one communication port and receives the test signal in a first communication port and sends it back via one or more other ports. The loopback module may include, for example, switches to route the test signal accordingly. The echoed signal received may then be compared against the original test signal to determine if the communication hardware is operating properly on the UDPD. In some instances, the timing of the test signal may also be tested to see if the test signal is transmitted and returned in the expected time frame. It should be appreciated that, in some instances, the test routine for such loopback testing may be implemented as part of the communication and/or timing test routine. It should also be appreciated that, in some instances, the loopback back module may comprise hardware and/or software implemented within the UDPD.

Figure 8:
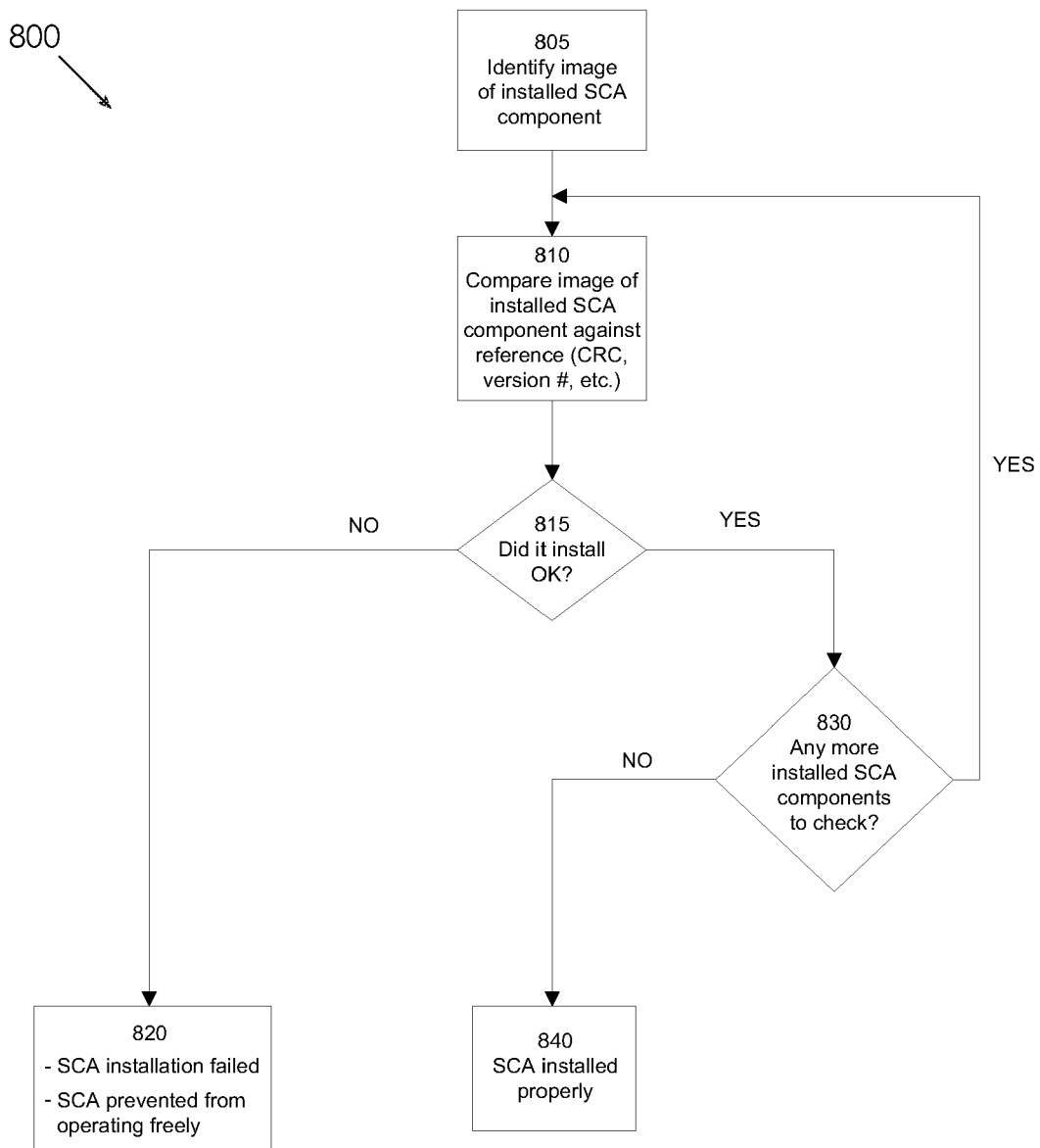
FIG. 8 illustrates a flow diagram for installation check, according to some aspects of the present disclosure.

FIG. 8 illustrates a flow diagram for an installation check, according to some aspects of the present disclosure. It should be understood that details discussed above for installation checks may be applicable to FIG. 8. As shown in FIG. 8, at block 805 of installation check 800, an image of an installed SCA component (e.g., one of a plurality of files for SCA 304 installed on UDPD 200) is identified. The image of an installed SCA component may include, for example, data about the installed SCA component, such as filename, version number, a cyclic redundancy value (CRC), etc.

At block 810, the image of the installed SCA component is compared to reference installation data corresponding to data that is expected for a proper installation. For example, a filename, CRC value, and/or version number associated with the installed SCA component may be compared with corresponding expected filename, CRC value, and/or version number in the reference installation data.

Based on the results of the comparison, a determination is made as to whether the installed SCA component was installed properly or not, as represented by block 815. For example, a determination may be made as to whether the image of each installed SCA component matches or does not match the reference installation data.

If, for example, the image of the installed SCA component does not match the reference installation data, then it is determined that SCA 304 failed to install properly on UDPD 200, as represented by block 820. SCA 304 may then be prevented from operating freely on UDPD 200. Again, in some instances, this may comprise disabling the SCA so that it is unable to be run on the UDPD. In some instances, this may comprise permitting the SCA to operate so that the user may still use non-safety critical features of the SCA but unable to use the safety critical features. In some instances, the failure to install properly is reported (e.g., logged and/or communicated to the user of the UDPD, etc.). In some instances, a report of the failure may be sent to a remote device—e.g., via the internet.

If, for example, the image of the installed SCA component matches the reference installation data, then it is determined that the installed SCA component installed properly on UDPD 200 and a determination is made as to whether there are any additional images of installed SCA components that require checking, as represented by block 830.

If there are additional images of installed SCA components that require checking, the next installed SCA component is identified and the process repeated for the next installed SCA component, as represented by the arrow returning to block 810. This process is repeated until all installed SCA components that are required to be checked have been identified and determined if installed properly.

When no additional installed SCA components are remaining, and all installed SCA components are determined to be installed properly, the installation checks 412 indicates that SCA 304 was installed properly on UDPD 200, as represented by block 840. In some instances, the proper installation of SCA 304 is reported (e.g., logged and/or communicated to the user of UDPD 200, etc.). In some instances, a report of the proper installation may be sent to a remote device—e.g., via the internet.

Figure 9:
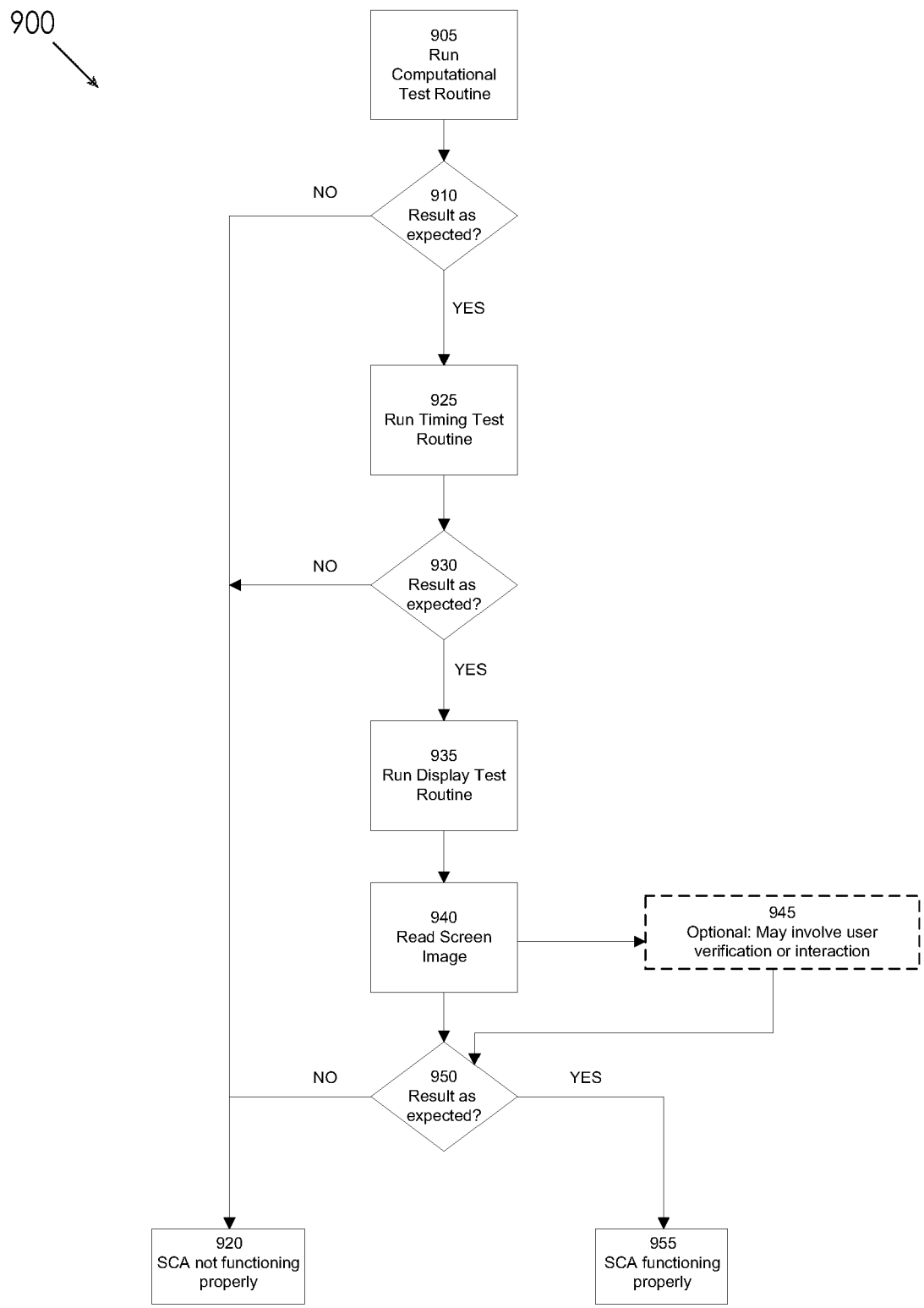
FIG. 9 illustrates a flow diagram for a functional check, according to some aspects of the present disclosure.

FIG. 9 illustrates a flow diagram for a functional check, according to some aspects of the present disclosure. It should be understood that details discussed above for functional check may also be applicable to FIG. 9. As shown in FIG. 9, at block 905 of functional check 900, one or more computational test routines are run to determine whether SCA 304 is performing computations accurately on UDPD 200. For example, reference computational input are provided to SCA 304 and specific safety critical computations are initiated by SCA 304 on UDPD 200 using the reference computational input. The results of the computations are compared with reference computational data to determine if the results fall within predetermined parameters and requirements defined by reference computational data.

Again, specific computations may vary depending on the specific safety critical features implemented within SCA 304. Computations may include, for example, various calculations, measurements, extrapolations, etc., for a wide variety of applications, such as medical applications and other SCAs. For example, computations for analyte monitoring applications may include, but are not limited to, computing analyte (e.g., glucose) measurements, calculating medicine dosages and/or administration times (e.g., insulin dosages from received glucose measurements), executing various other therapy-related algorithms (e.g., trending calculations, various alert determinations, etc.), and/or other safety critical computations that are applicable to the specific SCA implemented.

At block 910, a determination is made as to whether the results of the computations match or do not match the reference computational data. If the results do not fall within the reference computational data, then it is determined that SCA 304 does not perform the computations accurately. This indicates that SCA 304 is not functioning properly on UDPD 200, and thus not operating properly on UDPD 200. SCA 304 may then be prevented from operating freely on UDPD 200, as represented by block 920. If the results do fall within the reference computational data, then SCA 304 performs the computations accurately on UDPD 200 and one or more timing test routines are run, as represented by block 925.

At block 925, the times it takes to perform various activities (e.g., computations of block 905) on UDPD 200 are determined and compared with reference timing data. For example, timing test routines 532 may determine the time it takes for SCA 304 to perform computations initiated by computational test routines 530. In some instances, for example, time stamps or logs of particular events or duration of events may be recorded. For example, various times associated with the execution of computational test routines 530 may be logged or recorded—e.g., the time when reference computational input is provided to SCA 304, and the time when corresponding results are provided by SCA 304 (the difference of the two times representing the time it took SCA 304 to perform the computation on UDPD 200). In some instances, new activities are performed and the beginning and ending times are recorded such that the duration of the activity is determined. It should be appreciated that a timer may also be implemented or any other suitable method of tracking time.

At block 930 a determination is made as to whether the times to perform the activities (e.g., computations of block 905) fall within the reference timing data. If, for example, the times do not fall within the reference timing data, then SCA 304 does not perform the computations in a timely manner on UDPD 200, indicating that SCA 304 is not functioning properly on UDPD 200, and thus not operating properly on UDPD 200. SCA 304 may then be prevented from operating freely on UDPD 200, as represented by block 920. If, for example, the times to perform the activities (e.g., computations of block 905) do fall within the reference timing data, then SCA 304 performs the computations in a timely manner on UDPD 200 and one or more display test routines may be run, as represented by block 935.

At block 935, specific predetermined images defined by reference display inputs are initiated to be displayed on the display of UDPD 200. The actual image displayed is identified, as represented by block 940. For example, a screen capture may be initiated to identify the actual image displayed. Any form of data may be displayed on the display as desired (e.g., pixel patterns, image files (jpeg, etc.), text, numerals, etc.). In some instances, the reference display inputs corresponds to an expected result of a computation performed at block 905 that is to be displayed on the display. In some instances, a display pattern may be used. The actual image displayed is then compared to reference display data to determine if the actual images displayed on UDPD 200 matches or does not match the reference display data, as represented by block 950.

At optional block 945, user verification or interaction is also required. The user may be prompted, for example, to confirm that UDPD displays data properly. For example, the user may be prompted to enter the numeral, text, or phrase that is displayed; or to provide any other form of confirmation response to the image shown on the display; etc. Based on whether a valid user confirmation is received, it is determined if the reference display inputs is properly displayed on UDPD 200.

At block 950, a determination is made as to whether the actual image displayed on UDPD 200 is displayed properly (e.g., within the predetermined parameters and requirements defined by the reference display data). For example, the reference display data may include data representing the expected or correct image of the screen capture. The actual image displayed is compared to the reference display data to determine whether the actual image displayed matches or does not match the reference display data. Furthermore, the reference display data may include the expected or valid user confirmation that is to be received for user confirmation that the UDPD displays data properly.

If, for example, the actual image displayed (e.g., determined either from the screenshot or from user confirmation) does not match the reference display data, then SCA 304 is not functioning properly on UDPD 200, which indicates that SCA 304 is not operating properly on UDPD 200. The SCA is then prevented from operating freely on the UDPD, as represented by block 920. If, for example, the actual image displayed (and user confirmation) matches the reference display data, then SCA 304 is functioning properly on UDPD 200, as represented by block 955.

Figure 10:
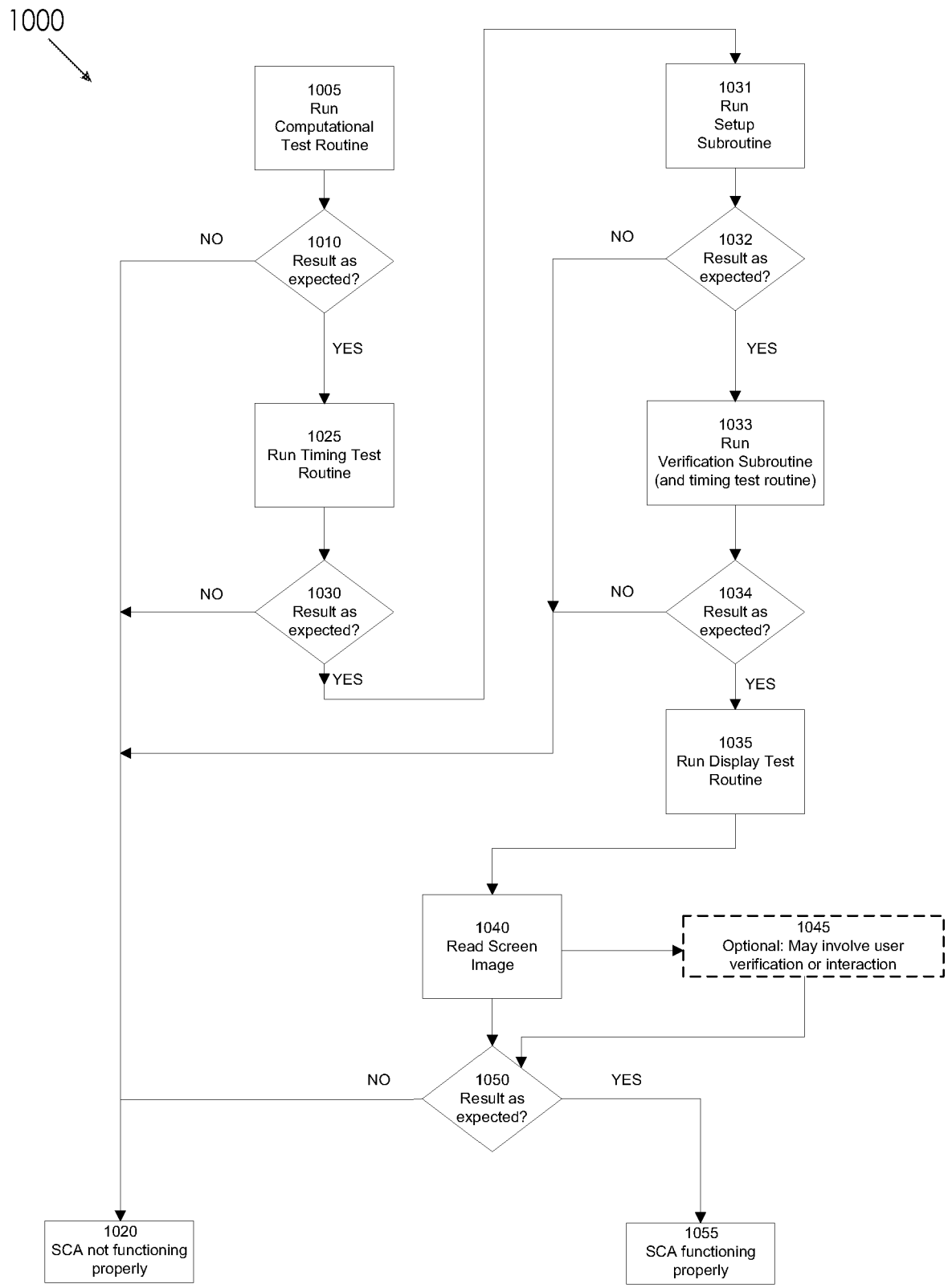
FIG. 10 illustrates a flow diagram for a functional check, according to some aspects of the present disclosure.

FIG. 10 illustrates a flow diagram for a functional check, according to some aspects of the present disclosure. The embodiment shown in FIG. 10 is similar to the functional check described in FIG. 9 except that the embodiment shown in FIG. 10 includes communication test routines. For the sake of clarity and brevity, the duplicative description in FIG. 9 has been condensed in great detail for FIG. 10, and it should be understood that the description above for similar blocks in FIG. 9 apply to FIG. 10 as well.

At block 1005 of functional check 1000, one or more computational test routines are executed. Reference computational inputs are provided to SCA 304 and specific safety critical computations are initiated by SCA 304 on UDPD 200 using the reference computational input. The results of the computations are compared with reference computational data to determine if the results fall within predetermined parameters and requirements defined by reference computational data.

At block 1010, a determination is made as to whether the results of the computations match or do not match the reference computational data. If, for example, the results do not fall within the reference computational data, then it is determined that SCA 304 does not perform the computations accurately, indicating that SCA 304 is not functioning properly on UDPD 200, and thus not operating properly on UDPD 200. SCA 304 may then be prevented from operating freely on UDPD 200, as represented by block 1020. If, for example, the results do fall within the reference computational data, then SCA 304 performs the computations accurately on UDPD 200 and one or more timing test routines are run, as represented by block 1025.

At block 1025, the times it takes to perform various activities (e.g., computations of block 1005) on UDPD 200 are determined and compared with reference timing data. In some instances, the times to perform the computations of block 1005 are determined. For example, the beginning and ending times of the computations may have been recorded—e.g., when the reference computational input was provided, and when a result was determined. In some instances, new activities are performed and the beginning and ending times are recorded such that the duration of the activity is determined.

At block 1030 a determination is made as to whether the times to perform the activities (e.g., computations of block 1005) fall within the reference timing data. If, for example, the times do not fall within the reference timing data, then SCA 304 does not perform the computations in a timely manner on UDPD 200, indicating that SCA 304 is not functioning properly on UDPD 200, and thus not operating properly on UDPD 200. SCA 304 may then be prevented from operating freely on UDPD 200, as represented by block 1020. If, for example, the times to perform the activities (e.g., computations of block 1005) do fall within the reference timing data, then SCA 304 performs the computations in a timely manner on UDPD 200 and one or more communication test routines may be run, as represented by block 1031.

At block 1031, communication test routines are initiated to determine whether SCA 304 communicates properly between UDPD 200 and an external device. At block 1031, setup subroutines are initiated to determine whether SCA 304 may properly establish a communication link between UDPD 200 and an external device. Setup subroutines initiate SCA 304 to establish a communication link between UDPD 200 and an external device.

At block 1032, a determination is made as to whether SCA 304 properly established a communication link between UDPD 200 and an external device. If, for example, it is determined that SCA 304 may not properly establish a communication link between UDPD 200 and an external device, then communication setup subroutines indicate that SCA 304 does not communicate properly between UDPD 200 and the external device, which further indicates that SCA 304 does not function properly on UDPD 200, which further indicates that SCA 304 does not operate properly on UDPD 200. SCA 304 may then be prevented from operating freely on UDPD 200, as represented by block 1020.

If, for example, it is determined that SCA 304 may properly establish a communication link between UDPD 200 and an external device, then verification subroutines are run, as represented by block 1033. Verification subroutines determine whether SCA 304 communicates (e.g., send and/or receive data) accurately over the communication link between UDPD 200 and the external device—e.g., within predetermined parameters and requirements defined by reference communication data.

Specific SCA communications are initiated between UDPD 200 and the external device using reference communication inputs (e.g., test signal, echo signal, request for data, etc.). The actual results of the communications (e.g., echo signal received, response to a test signal, the confirmation signal received, the data received in response to a request for data, the expected value, the type of data received, the communication protocol used, any combination thereof, etc.) is compared with the reference communication data. In some instances, the reference communication data may be the same as the reference communication inputs—e.g., when an echo signal is implemented.

A determination is made as to whether the actual results of the communication match or do not match the reference communication data, as represented by block 1034. If, for example, it is determined that the actual results of the communication do not match the reference communication data, then SCA 304 does not communicate accurately over the communication link between UDPD 200 and the external device, which indicates that SCA 304 does not communicate properly between UDPD 200 and the external device, which further indicates that SCA 304 does not function properly on UDPD 200, which further indicates that SCA 304 does not operate properly on UDPD 200. SCA 304 may then be prevented from operating freely on UDPD 200, as represented by block 1020.

At block 1033, optional timing test routines may also be run to determine whether SCA 304 performs communications on UDPD 200 with an external device in a timely manner—e.g., within times falling within "reference timing data" that represent a certain level of confidence that SCA 304 is communicating in a timely manner on UDPD 200 with an external device. For example, the time it takes for SCA 304 to properly establish a communication link between UDPD 200 and an external device in block 1031 may be determined; and/or the time it takes to perform the communications initiated in block 1033 may be determined.

At block 1034 a determination is made as to whether SCA 304 performs the communication in a timely manner (e.g., whether the time it takes to perform the communications initiated in block 1033 matches the reference timing data). If, for example, it is determined that SCA 304 does not perform the communication in a timely manner (e.g., the time does not match the reference timing data) on UDPD 200, then a determination is made that the SCA 304 does not communicate properly on UDPD 200, which indicates that SCA 304 does not function properly on UDPD 200, which further indicates that SCA 304 is not operating properly on UDPD 200. SCA 304 may then be prevented from operating freely on UDPD 200, as represented by block 1020.

If, for example, it is determined that the actual results of the communication matches the reference communication data, then SCA 304 communicates accurately over the communication link between UDPD 200 and the external device. Further, if the time to perform the communication matches the reference timing data, then it is determined that SCA 304 performs the communication in a timely manner on UDPD 200.

At block 1035, display test routines are run. Upon execution of display test routines, specific predetermined images defined by reference display inputs are initiated to be displayed on the display of UDPD 200. The actual image displayed is identified, as represented by block 1040. For example, a screen capture may be initiated to identify the actual image displayed. In some instances, the reference display inputs corresponds to an expected result of a computation performed at block 1005 that is to be displayed on the display. The actual image displayed is then compared to reference display data to determine if the actual images displayed on UDPD 200 matches or does not match the reference display data, as represented by block 1050.

At optional block 1045, user verification or interaction is also required. The user may be prompted, for example, to confirm that UDPD displays data properly. For example, the user may be prompted to enter the numeral, text, or phrase that is displayed; or to provide any other form of confirmation response to the image shown on the display; etc. Based on whether a valid user confirmation is received, it is determined if the reference display inputs is properly displayed on UDPD 200. In some instances, the display testing may involve the remote device. For example, the user could be asked to confirm the existence of, or reenter, displayed information on the remote display to confirm the overall functionality. A code may be displayed on the display of the remote device, for example, and the user prompted to reenter the code on the remote device.

At block 1050, a determination is made as to whether the actual image displayed on UDPD 200 is within the predetermined parameters and requirements defined by the reference display data. If, for example, the actual image displayed (and/or user confirmation) does not match the reference display data, then SCA 304 is not functioning properly on UDPD 200, which indicates that SCA 304 is not operating properly on UDPD 200. The SCA is then prevented from operating freely on the UDPD, as represented by block 1020. If, for example, the actual image displayed (and user confirmation) matches the reference display data, then SCA 304 is determined to be functioning properly on UDPD 200, as represented by block 1055.

Figure 11:
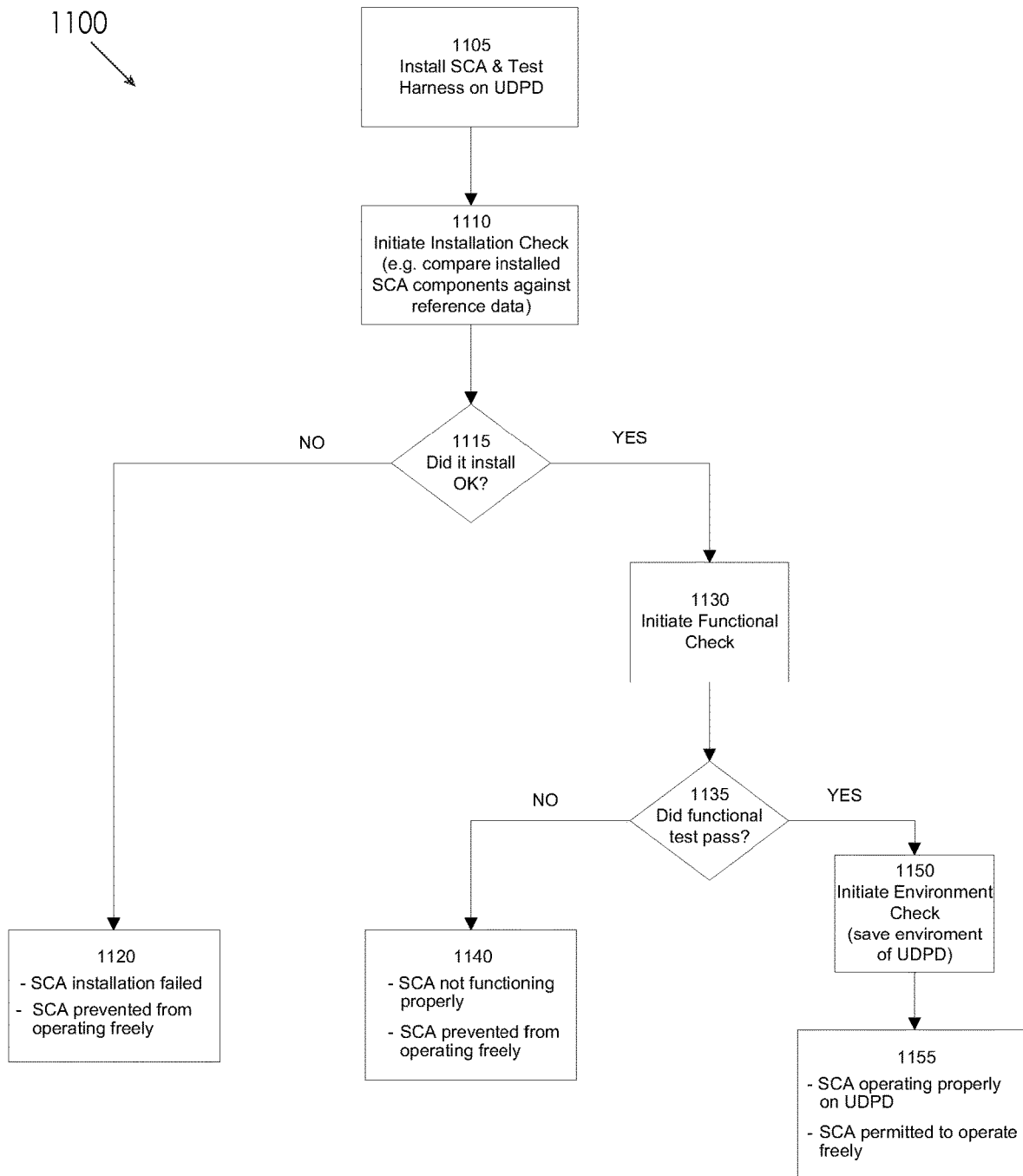
FIG. 11 illustrates a flow diagram for an installation process, according to some aspects of the present disclosure.
Figure 12:
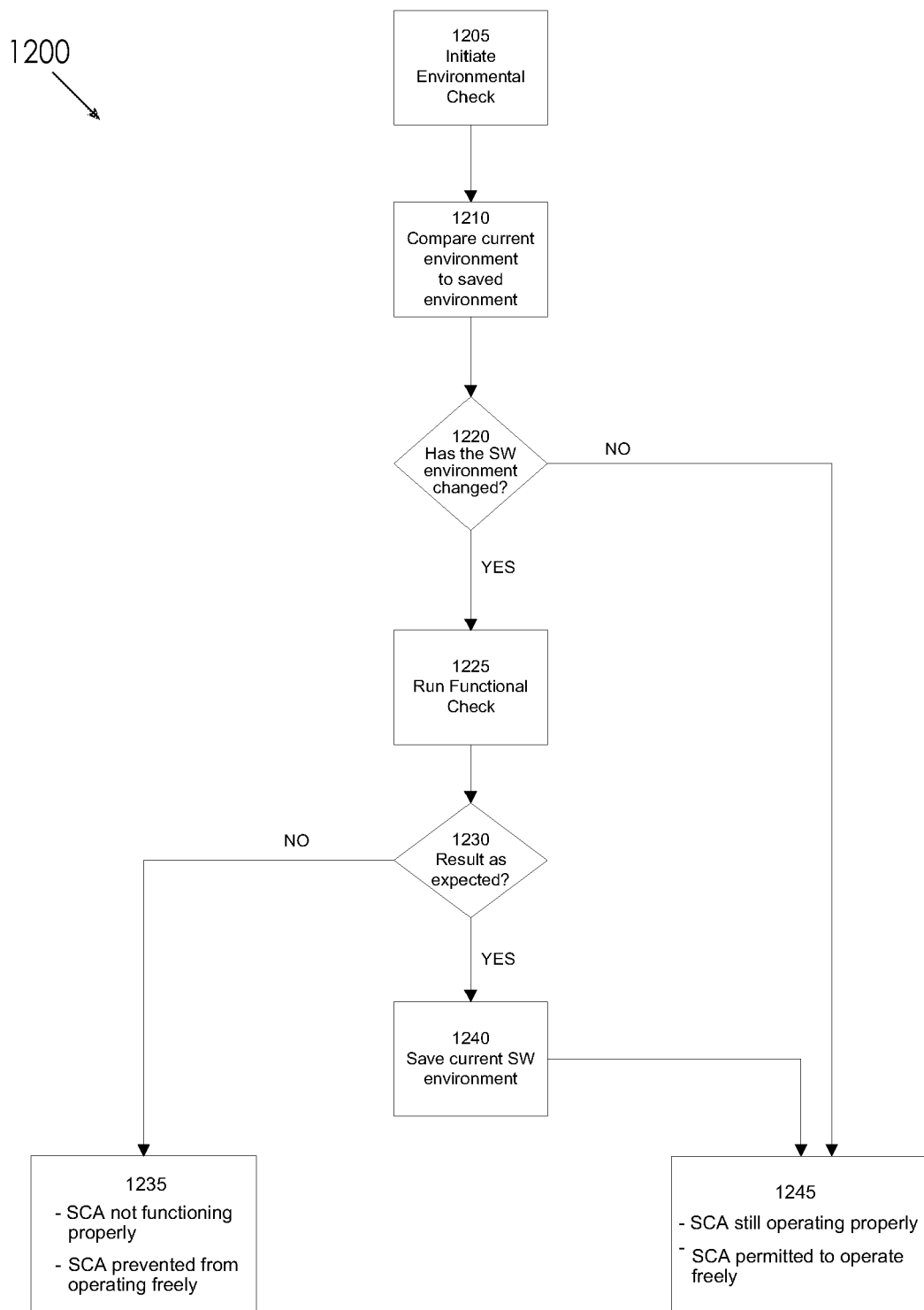
FIG. 12 illustrates a flow diagram for a process for performing checks, according to some aspects of the present disclosure.

It should be appreciated that in some embodiments the above checks may be executed at various times and in various combinations to achieve different levels of confidence that the SCA is operating properly on the UDPD. FIGS. 11 and 12 illustrate example flow diagrams for hosting a SCA on a UDPD, according to some aspects of the present disclosure. The discussion above for the various checks, test routines, and subroutines are also applicable to FIGS. 11 and 12.

FIG. 11 illustrates a flow diagram for an installation process, according to some aspects of the present disclosure. At block 1105 of process 1100, SCA 304 and test harness 310 are installed on UDPD 200. In some instances, SCA 304 may be initially prevented from freely operating on UDPD 200 to ensure that the following initial checks are first performed before the user uses SCA 304.

At block 1110, an installation check is initiated. For example, in some, the installation test identifies and compares images of installed SCA components with reference installation data. It should be appreciated that in some instances, the installation check also determines whether the test harness was also installed properly on UDPD 200.

Based on the results of the installation test performed (e.g., whether images of installed SCA components matches or does not match reference installation data), a determination is made as to whether SCA 304 installed properly, as represented by block 1115. If, for example, it is determined that SCA 304 did not install properly on UDPD 200 (e.g., whether images of installed SCA components matches or does not match reference installation data), the failure to install properly is reported and the SCA prevented from operating freely—e.g., disabling SCA 304 so that it is unable to run on UDPD 200, as represented by block 1120. For example, the installation failure may be logged and/or reported to the user. In some instances, test harness 310 may send a report of the failure to a remote device—e.g., via the internet. Again, in other instances, SCA 304 may be permitted to operate so that the user may still use functions of SCA 304 that are not safety critical.

If, for example, it is determined at block 1115 that SCA 304 installed properly on UDPD 200, a functional test is run to determine whether SCA 304 is functioning properly on UDPD 200, as represented by block 1130. As described earlier, functional test may include one or more test routines which may be executed—e.g., the computational test routines, timing test routines, display test routines, and/or communication test routines.

At block 1135, a determination is made as to whether SCA 304 functions properly on UDPD 200. For example, functioning properly may require a determination that SCA 304 is computing accurately on UDPD 200, that SCA 304 is performing activities (e.g., computations) in a timely manner on UDPD 200, that data for SCA 304 is displayed properly on UDPD 200, and/or that SCA 304 may communicate properly (e.g., may establish a function communication link and send/receive test data in a timely manner) with an external device via a communication link between the external device and UDPD 200.

If, for example, it is determined that SCA 304 does not function properly on UDPD 200, then it is determined that SCA 304 is not operating properly on UDPD 200 and SCA 304 may then be prevented from operating freely on UDPD 200, as represented by block 1140.

If, for example, SCA 304 functions properly, then it is determined that SCA 304 is operating properly on UDPD 200 and an environment check is executed to determine and save the current environment of UDPD 200 that is associated with the determination that SCA 304 is operating properly, as represented by block 1150. SCA 304 may then be allowed to operate freely on UDPD 200. Furthermore, it should be appreciated that the checks may be initiated in different orders in other implementations.

FIG. 12 illustrates a flow diagram for an exemplary process for performing various checks, according to some aspects of the present disclosure. The flow diagram of FIG. 12 may, for example, occur at runtime after SCA 304 has already been permitted to operate freely (e.g., after the process described in FIG. 11 has been run). It should be appreciated that the process may be run in the background on UDPD 200 in some instances. For example, process 1200 may be run in the background while SCA 304 is being run, in the background when SCA 304 is not being run, in the background while other applications are being run in the foreground, etc. Furthermore, it should be appreciated that process 1200 may be transparent to the user.

At block 1205 of process 1200, an environment check is initiated to determine if the 'current environment' of UDPD 200 has changed since the last determination that SCA is operating properly and permitted to operate freely on UDPD 200. Environment check may be initiated at various times— e.g., at predetermined times/intervals (e.g., predetermined time intervals after SCA is permitted to operate freely on the UDPD), and/or upon occurrences of certain events such as when SCA is run, after SCA is closed, etc.

Environment check identifies the current environment— e.g., any currently installed software programs, applications, drivers, hardware components, etc. At block 1210, the current environment is then compared to a previously stored 'current environment' that was associated with the last determination that SCA 304 is operating properly on UDPD 200. For example, the comparison may determine if the current environment matches or does not match the previously stored current environment. It should be appreciated that not only newly installed programs may be accounted for, but also removed programs and/or modifications to programs (e.g., new revision updates, software fixes, firmware updates, etc.). In some embodiments, only the software environment may be taken into consideration. In other embodiments, the hardware environment may also be taken into consideration.

Based on the comparison in block 1210, a determination is made as to whether the environment of UDPD 200 has been changed since the last determination that SCA 304 is operating properly on UDPD 200 and permitted to operate freely on UDPD, as represented by block 1220.

If, for example, it is determined that the environment of UDPD 200 has not changed, then a certain level of confidence is achieved that SCA 304 is still operating properly on UDPD 200. SCA 304 may, for example, be permitted to continue operating freely, as represented by block 1245. It is contemplated that in some instances, if the environment has not changed, functional checks may still be initiated, in full or an abbreviated set, to provide greater assurance that SCA 304 is operating properly.

If, for example, it is determined that the environment of UDPD 200 has changed, then SCA 304 may potentially operate improperly on UDPD 200 and a functional check is initiated, as represented by block 1225. For example, computational test routines, timing test routines, display test routines, and/or communication test routines may be run to determine if SCA 304 is functioning properly on UDPD 200. In some instances, SCA 304 is permitted to continue to operate freely while the functional check is performed. In some instances, SCA 304 is prevented from operating freely while the functional check is performed. In other implementations, an installation check may also be initiated if the environment has changed.

At block 1230, a determination is made as to whether SCA 304 functions properly on UDPD 200. For example, functioning properly may require a determination that SCA 304 is computing accurately on UDPD 200, that SCA 304 is performing activities (e.g., computations) in a timely manner on UDPD 200, that data for SCA 304 is displayed properly on UDPD 200, and/or that SCA 304 may communicate properly (e.g., may establish a function communication link and communicate data accurately and in a timely manner) with an external device via a communication link between the external device and UDPD 200.

If, for example, it is determined that SCA 304 does not function properly on UDPD 200, then it is determined that SCA 304 is not operating properly on UDPD 200 and SCA 304 may then be prevented from operating freely on UDPD 200, as represented by block 1235. If, for example, it is determined that SCA 304 functions properly, then the current environment of UDPD 200 is saved, as represented by block 1240. SCA 304 is determined that SCA 304 is operating properly on UDPD 200 and SCA 304 is permitted to operate freely on UDPD 200, as represented by block 1245. The process may be repeated again at another time and/or occurrence of an event.

In some aspects of the present disclosure, UDPD 200 may include a host integrity check that is executed to determine if the integrity of SCA 304 has been corrupted because a corrupted SCA 304 compromises any assurance that SCA 304 operates properly on UDPD 200. In some instances, a determination that SCA 304 operates properly on UDPD 200 requires a determination that SCA 304 is not corrupted. If SCA 304 is corrupted, it may be determined that SCA 304 does not operate properly on UDPD 200 and SCA 304 may be prevented from operating freely on UDPD 200. If SCA 304 is determined to be uncorrupted, it may be determined that SCA 304 operates properly and permitted to operate freely, as long as any other required checks performed, or to be performed, are successfully passed as well.

Figure 13:
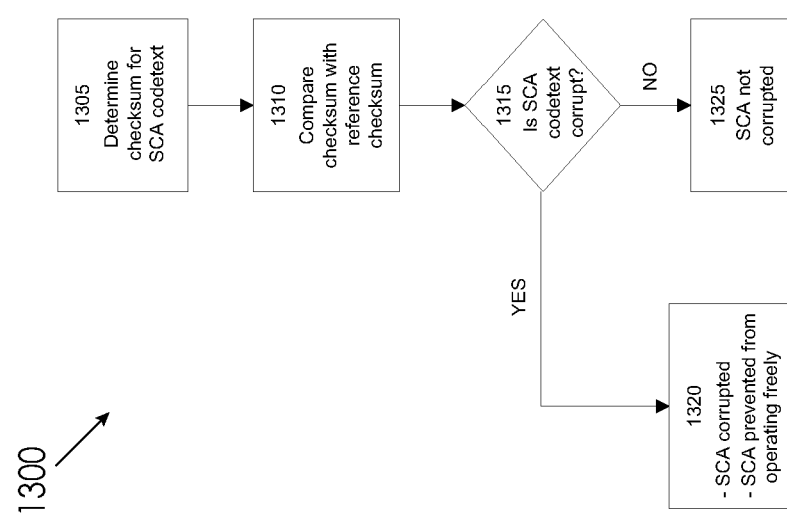
FIG. 13 illustrates a flow diagram for a host integrity check, according to some aspects of the present disclosure.

In some instances, the host integrity check is provided and may determine whether the codetext of SCA 304 is intact and uncorrupted. FIG. 13 illustrates a flow diagram for a host integrity check, according to some aspects of the present disclosure. At block 1305 of check 1300, a checksum for SCA 304 codetext is calculated. In addition to SCA 304 codetext, the host integrity check may also check the integrity of other nonvolatile and critical data associated with SCA 304—e.g., data that SCA 304 require or uses, such as reference data for various checks. The calculated checksum is then compared against a reference checksum, as represented by block 1310. The reference checksum is a checksum for SCA 304 codetext (and/or additional data associated with SCA 304) in an uncorrupted state (e.g., a checksum calculated previously during manufacturing and testing and stored as a reference checksum for later integrity checks). In some instances, the reference checksum may be stored as part of reference data 408. At block 1315, it is determined based on the comparison whether SCA 304 codetext is corrupted. For example, if the calculated checksum matches the reference checksum, then it is determined that SCA 304 is uncorrupted. On the other hand, if the calculated checksum does not match the reference checksum, then it is determined that SCA 304 is corrupted. If the calculated checksum does not match the reference checksum, then SCA 304 is determined to be corrupted and SCA 304 is prevented from operating freely, as represented by block 1320. If SCA 304 is determined to be uncorrupted, then SCA 304 is permitted to operate freely as long as any other required checks performed, or to be performed, are successfully passed.

In some embodiments, the host integrity check may be implemented as a test module that resides on UDPD 200 in non-volatile memory. The host integrity test may be stored on UDPD 200 through any variety of methods. For example, the host integrity check may be provided to UDPD 200 via the internet, from CD-ROM, memory stick, other external memory device, etc. In some instances, the host integrity check may be provided on an installation device (e.g., installation CD-ROM) that includes the test harness and/or SCA 304. In some instances, the host integrity check may be included as part of the test harness and stored on UDPD 200 when the test harness is loaded on UDPD 200.

The host integrity test may be programmed to initiate at various times. In some instances, the host integrity test may be initiated at non-runtimes. For example, the host integrity check may be programmed to initiate every time before SCA 304 is run, periodically after a predetermined amount of time, whenever the software environment has changed, etc.

In some embodiments, the host integrity check may be initiated as part of an installation process. For example, in FIG. 11, in some instances, the host integrity check may be initiated before, after, or simultaneously with functional check 1130 in process 1100. Therefore, in addition to expected results for the installation check and functional checks, block 1155 would also require expected results for the host integrity check (e.g., that SCA 304 codetext is uncorrupted). If the host integrity check results in unexpected results (e.g., SCA 304 codetext is corrupted), then SCA 304 is prevented from operating freely. Thus, process 1100 would determine if SCA 304 installed correctly, if the integrity of SCA 304 maintained, and if SCA 304 functions properly. It should be understood that additional checks may also be included—e.g., the coexistence check, interoperability test, power management test, etc.

In some embodiments, the host integrity check may be programmed to initiate when the software environment has changed. For example, in FIG. 12, in some instances, the host integrity check may be initiated before, after, or simultaneously with functional check 1225 in process 1200. Therefore, in addition to expected results for the functional check, block 1245 would also require expected results for the host integrity check (e.g., that SCA 304 codetext is uncorrupted). If the host integrity check results in unexpected results (e.g., SCA 304 codetext is corrupted), then SCA 304 is prevented from operating freely. Thus, process 1200 would determine if the environment changed, if the integrity of SCA 304 is still maintained, and if SCA 304 still functions properly. It should be understood that additional checks may also be included—e.g., the coexistence check, interoperability test, power management test, etc.

In some aspects of the present disclosure, a coexistence check may be initiated to determine if SCA 304 is incompatible with other programs on UDPD 200 as relates to the safety critical nature of SCA 304. In some instances, a determination that SCA 304 operates properly on UDPD 200 requires at least a determination that SCA 304 is not incompatible with non-related programs. If SCA 304 is incompatible with one or more nonrelated programs, then SCA 304 may be prevented from operating freely on UDPD 200. If SCA 304 is not incompatible with any nonrelated programs, then it may be determined that SCA 304 operates properly and thus permitted to operate freely on UDPD 200, as long as any other required checks performed, or to be performed, are successfully passed as well.

It should also be noted that various programs may be in different states on UDPD 200—e.g., not running, in a passive state, in an active state, etc. To run a program, for example, UDPD 200 may load the program into volatile memory (e.g., RAM) and then execute the program. In some instances, when a program is invoked, the program is run on UDPD 200 in an active state. In other instances, a program may be brought up partially but not actively running. The program may remain in this passive state and wait for an invocation to bring the program into an active state. For example, some programs need to be "alive" even though they are not actively running—e.g., to update time, periodically monitor devices, to monitor for communications, etc. Safety critical incompatibilities may exist between SCA 304 and non-related programs when either, or both, of the programs are in either an active or passive state.

The coexistence check identifies whether any safety critical incompatibilities exist between SCA 304 and another application in their active and/or passive states. If an incompatibility exists, the appropriate action may be taken—e.g., SCA 304 may be prevented from operating freely on UDPD 200. In some instances, the user may be alerted to the incompatibility and requested not to use the incompatible program or to disable or uninstall the incompatible program.

Figure 14:
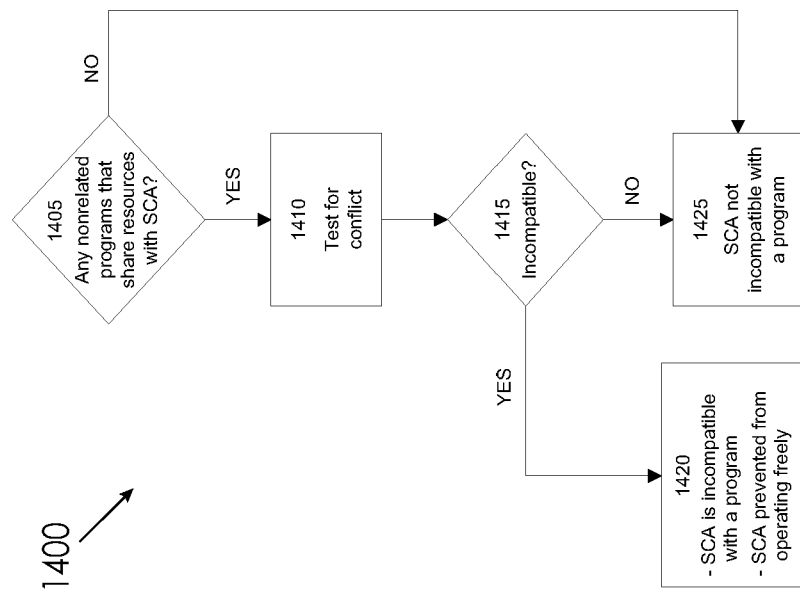
FIG. 14 illustrates a flow diagram for a coexistence check, according to some aspects of the present disclosure.

FIG. 14 illustrates a flowchart for a coexistence check, according to some aspects of the present disclosure. At block 1405 of check 1400, it is determined if any nonrelated programs share any resources with SCA 304. If no resources are shared, then SCA 304 is not incompatible with any nonrelated programs, as represented by block 1430. If SCA 304 shares resources with one or more nonrelated programs, then it is determined if the sharing of resources compromises the safety critical aspect of SCA 304 by creating a conflict, as represented by block 1410. For example, the coexistence check may initiate a conflict scenario between SCA 304 and the one or more non-related related programs, sequentially or simultaneously. The conflict scenario may comprise, for example, bringing up SCA 304 and nonrelated application and having each attempt to access the shared resource at the same time. For instance, the conflict scenario may include a nonrelated application and SCA 304 attempting to simultaneously use wireless communication, simultaneously display information to the display of UDPD 200, simultaneous read and/or write to memory, etc. As another example, the SCA may access a resource first and subsequently thereafter, a nonrelated program attempt to access the same resource—or vice versa. Moreover, as another example, if UDPD 200 is a mobile phone or smartphone, a conflict scenario may be initiated to test how an incoming call received by UDPD 200 impacts SCA 304 while performing various functions—e.g., a data transfer by SCA 304, a display of a test measurement by SCA 304, a sounding of an alarm by SCA 304, etc.

In some instances, the SCA 304 may share resources with other programs without creating a conflict. For instance, the SCA 304 may have priority access to resources in certain circumstances and thus take priority over other programs using the same resources. For example, SCA 304 may be given priority access to communication ports on the UDPD 200—e.g., to communicate an alarm to another device via the communication port. SCA 304 may, for example, have priority access to a wireless communication device, to memory access, to processor access, and/or access to any other shared resource that may be prioritized. It should be appreciated that priority access for the SCA 304 may also comprise priority access for communications to or for the SCA 304. For example, a medical device (e.g., analyte monitoring device, drug administration device, etc.) may send a query from the medical device to the UDPD 200 (or vice versa) which, when operating properly, interrupts processes currently running on the UDPD 200 in order to in order to create a transmission between the two devices (e.g., verifying readiness to receive data, waiting for a response, communicating the data if the response is received and activating an alarm if the response is not received). The coexistence check may initiate various conflict scenarios to test the sharing of resources and determine if the SCA 304 is properly accessing the resources with priority over other programs trying to access the same resource.

It should be understood that the each program may be brought up to different states (e.g., passive or active) to determine if any safety critical issues are posed in any of the various combinations of states. Further, it should be understood that in some instances, a conflict scenario may include more than one nonrelated program and SCA 304 accessing the same shared resource.

At block 1415, it is determined if SCA 304 and any nonrelated programs are incompatible. For example, if a nonrelated program is made to access the shared resource while SCA 304 is already accessing the resource, then it may be determined if the attempted access by the nonrelated program sufficiently disrupts the access by SCA 304 to compromise the safety critical nature of SCA 304. Or, for example, if SCA 304 is made to access the shared resource while the nonrelated program is already accessing the resource, then it may be determined if SCA 304 can access the resource and whether it can do so sufficiently so as to not compromise the safety critical nature of SCA 304. If SCA 304 cannot share resources with the nonrelated program without compromising the safety critical aspects of SCA 304, then SCA 304 and nonrelated program are determined to be incompatible and SCA 304 prevented from operating freely, as represented by block 1420. For example, if the conflict scenario prevents SCA 304 from performing any safety critical function, or significantly delays SCA 304 from performing the safety critical function, then the nonrelated application and SCA 304 may be determined to be incompatible. It should be appreciated that, in some instances, reference data to test incompatibility may be used for such determinations.

SCA 304 may be prevented from operating freely, as described earlier for previous checks (e.g., SCA disabled and prevented from running on UDPD 200, SCA 304 permitted to operate but without the use of the safety critical features or capabilities, etc.). In addition, in some instances, SCA 304 may be permitted to operate without the use of the resource and/or feature that is in conflict with the nonrelated program. For example, if the shared resource in conflict is the Bluetooth receiver, then SCA 304 may be permitted to operate without the function of Bluetooth communication and/or features requiring the Bluetooth communication. In some instances, the user may be informed of the issue and/or prompted to address the issue—e.g., informed not to run the incompatible program, prompted to uninstall or disable the incompatible nonrelated program before being permitted to use SCA 304, etc.

If SCA 304 can share resources with nonrelated programs without compromising the safety critical aspects of SCA 304, then it is determined that SCA 304 is not incompatible with nonrelated programs, as represented by block 1425. SCA 304 may then be determined to operate properly on UDPD 200 and permitted to operate freely on UDPD 200, as long as any other required checks performed, or to be performed, are successfully passed as well.

The coexistence test may be programmed to initiate at various times—e.g., runtimes and/or non-runtimes. For example, the coexistence check may be programmed to initiate every time before SCA 304 is run, periodically after a predetermined amount of time, whenever the software environment has changed, etc.

In some embodiments, the coexistence check may be initiated as part of an installation process. For example, in FIG. 11, a coexistence check may be initiated before, after, or simultaneously with functional check 1130 in process 1100. Therefore, in addition to expected results for the installation check and functional check, block 1155 would also require expected results for the coexistence check (e.g., that SCA 304 is not incompatible with any nonrelated programs). If the coexistence check results in unexpected results (e.g., SCA 304 is incompatible with one or more nonrelated programs), then SCA 304 may be prevented from operating freely. Thus, process 1100 would determine if SCA 304 installed correctly, if SCA 304 is compatible with the nonrelated programs on UDPD 200, and if SCA 304 functions properly. It should be understood that additional checks may also be included—e.g., the host integrity check, interoperability test, power management test, etc.

In some embodiments, the coexistence check may be programmed to initiate when the software environment has changed. For example, in FIG. 12, the coexistence check may be initiated before, after, or simultaneously with functional check 1225 in process 1200. Therefore, in addition to expected results for the functional check, block 1245 would also require expected results for the coexistence check (e.g., that SCA 304 is not incompatible with other nonrelated programs). If the coexistence check results in unexpected results (e.g., SCA 304 is incompatible with a nonrelated program), then SCA 304 may be prevented from operating freely. Thus, process 1200 would determine if the environment changed, if SCA 304 is compatible with the nonrelated programs on UDPD 200, and if SCA 304 still functions properly. It should be understood that additional checks may also be included—e.g., the host integrity check, interoperability test, power management test, etc.

In some embodiments, a determination that SCA 304 operates properly on the UDPD requires a determination that SCA 304 interoperates properly with related programs. If SCA 304 does not interoperate properly with other related programs, then it may be determined that SCA 304 does not operate properly and SCA 304 may be prevented from operating freely on UDPD 200. If SCA 304 is determined to interoperate properly, then it may be determined that SCA 304 operates properly on the UDPD and thus permitted to operate freely, as long as any other required checks performed, or to be performed, are successfully passed as well.

Figure 15:
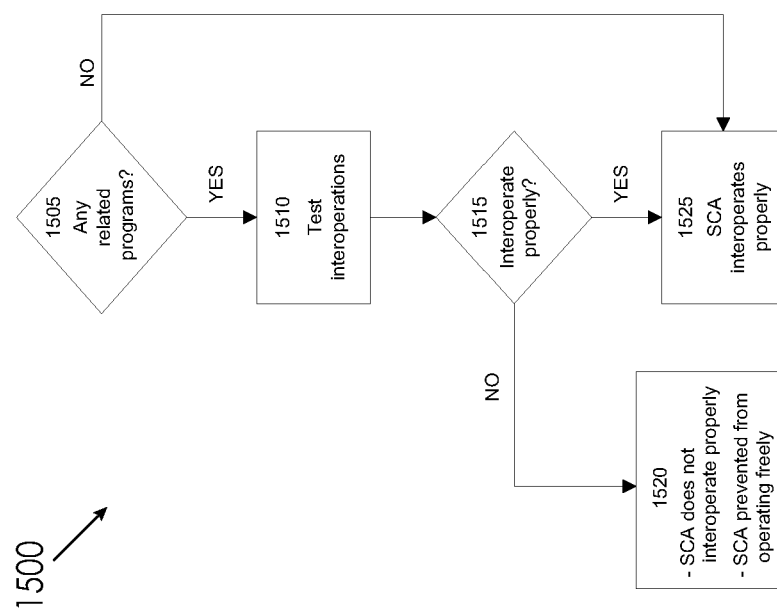
FIG. 15 illustrates a flow diagram for an interoperability check, according to some aspects of the present disclosure.

FIG. 15 illustrates a flowchart for an interoperability check, according to some aspects of the present disclosure. At block 1505 of check 1500, it is determined if any related programs work with SCA 304. If there are no related programs, then SCA 304 does not interoperate improperly with any related programs, as represented by block 1525. If related programs exist, then interoperability check tests the interoperations of the related program and SCA 304, as represented by block 1510 It should be appreciated that more than one related program may be tested at one time in some instances.

For example, one or more related programs and SCA 304 are brought up and tested for proper interoperations. The testing may include, for example, verifying that SCA 304 and programs communicate using the proper communication protocols, that data is being communicated back and forth accurately and in a timely manner, that SCA 304 can properly access any features or capabilities associated with the related program, etc.

For example, SCA 304 may be an application related to analyte monitoring and provide some data measurement and data management capabilities while an additional program may provide additional or more in-depth data management capabilities. SCA 304 may provide for the logging of measurements in memory on UDPD 200 and work in conjunction with an application that displays the logged measurements in different graphical formats (e.g., graphs, charts, etc.), for instance. The interoperability test may cross check, for example, values and times in the log with the corresponding values in the graphical displays to determine if the data transfers accurately.

As another example, SCA 304 may be an application related to analyte monitoring and interoperate with software programs for a remote sensor device, analyte meter, pump provider (e.g., insulin pump device), etc. The testing may include, for example, verifying that SCA 304 and related program communicate using the proper communication protocols, that data is being communicated back and forth accurately and in a timely manner, that SCA 304 can properly access any features or capabilities associated with the related program, etc. Reference data may be used, for example, as inputs to simulate specific runtime events and to verify results of the simulated events (e.g., with specific reference data associated with the simulated event).

While the interoperability check has been described separate from the functional check (e.g., communication test routine), it is nonetheless contemplated that the interoperability check may work with, or be implemented as part of the functionality test (e.g., communication test routine) in some instances, to provide some assurance that SCA 304 interoperates properly with external devices.

At block 1515, it is determined if SCA 304 and related program interoperates properly. If it is determined that SCA 304 and related program do not interoperate properly, then SCA 304 is prevented from operating freely, as represented by block 1520. SCA 304 may be prevented from operating freely, as described earlier (e.g., SCA disabled and prevented from running on UDPD 200, SCA 304 permitted to operate but without the use of the safety critical features or capabilities, etc.). In addition, in some instances, SCA 304 may be permitted to operate without the use of the related program or its functionality (e.g., if the related program is not critical or required for SCA 304 to operate). For example, if the related program is a program providing additional data management capabilities as described in the example above, then SCA 304 is permitted to operate but without the use of the related program or its functionality. In some instances, the user may be informed of the issue and/or prompted to address the issue—e.g., informed not to use the related program or its functionality, prompted to uninstall or disable the related program before being permitted to use SCA 304, etc.

If it is determined that SCA 304 and the related programs interoperate properly, as represented by block 1525, then SCA 304 is determined to operate properly on the UDPD and permitted to operate freely, as long as any other required checks performed, or required to be performed, are successfully passed as well.

It should be understood that the each program may be brought up to different states (e.g., passive or active) to determine if any interoperability issues are posed in any of the various combinations of states. Further, it should be understood that in some instances more than one related program may be tested with SCA 304 during the interoperability test.

The interoperability check may be programmed to initiate at various times—e.g., runtimes and/or non-runtimes. For example, the interoperability check may be programmed to initiate every time before SCA 304 is run, periodically after a predetermined amount of time, whenever the software environment has changed, etc.

In some embodiments, the interoperability check may be initiated as part of the installation process. For example, in FIG. 11, the interoperability check may be initiated before, after, or simultaneously with functional check 1130 in process 1100. Therefore, in addition to expected results for the installation check and functional check, block 1155 would also require expected results for the interoperability check (e.g., that SCA 304 interoperates properly with related programs). If the interoperability check results in unexpected results (e.g., SCA 304 does not interoperate properly with related programs), then SCA 304 is prevented from operating freely. Thus, process 1100 would determine if SCA 304 installed correctly, if SCA 304 interoperates properly with related programs on UDPD 200, and if SCA 304 functions properly. It should be understood that additional checks may also be included—e.g., the host integrity check, coexistence check, power management check, etc.

In some embodiments, the interoperability check may be programmed to initiate when the software environment has changed. For example, in FIG. 12, the interoperability check may be initiated before, after, or simultaneously with functional check 1225 in process 1200. Therefore, in addition to a expected results for the functional check, block 1245 would also require expected results for the interoperability check (e.g., that SCA 304 interoperates properly with related programs). If the interoperability check results in unexpected results (e.g., SCA 304 does not interoperate properly with a related program), then SCA 304 is prevented from operating freely. Thus, process 1200 would determine if the environment changed, if SCA 304 interoperates properly with related programs on UDPD 200, and if SCA 304 still functions properly. It should be understood that additional checks may also be included—e.g., the host integrity check, coexistence check, power management check, etc.

In some embodiments, a power management check may be initiated to determine if the power capabilities of UDPD 200 are sufficient to run SCA 304 safely with a certain level of assurance that the UDPD will not abruptly shutdown. For instances, the power capabilities may be determined from the remaining charge left on the battery, the current real-time power consumption rate (e.g., taking into account any applications running, features and capabilities activated, etc.), the time remaining until shutdown or hibernation, etc. The remaining power life of UDPD 200 may be determined in days, hours, minutes, etc., until needing to be recharged. Moreover, if a power hungry feature of SCA 304 is used (e.g., wireless capabilities, etc.), the remaining power life of UDPD 200 may be reduced accordingly. The power capabilities may then be compared to a minimum threshold amount required to operate SCA 304 safely with minimal risk of an abrupt shutdown.

Figure 16:
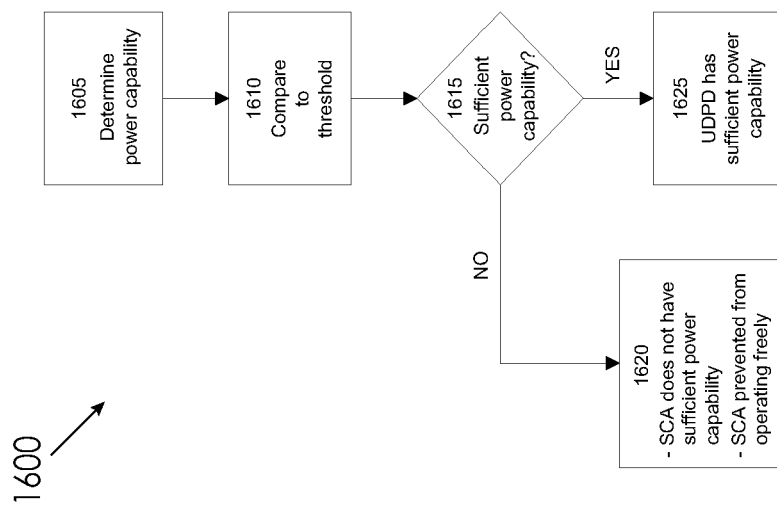
FIG. 16 illustrates a flow diagram for a power management check, according to some aspects of the present disclosure.

FIG. 16 illustrates a flow diagram for a power management check, according to some aspects of the present disclosure. At block 1605 of check 1600, the power capabilities of UDPD 200 are determined. Once the power capability of UDPD 200 is determined, a comparison is made against one or more minimum threshold amounts required to operate SCA 304 safely with minimal risk of abrupt shutdown, as represented by block 1610.

In some instances, the minimum threshold amount required to operate SCA 304 safely with minimal risk of abrupt shutdown may depend on a predetermined amount of time—e.g., determined during manufacturing and testing and stored as reference data. For example, testing may determine that SCA 304 requires a minimum threshold of time to operate and safely perform safety critical functions. Or, as another example, testing may determine that SCA 304 requires a certain amount of current per day, per hour, etc., when actively running. It is also contemplated that the different thresholds may exist for different features or functions (e.g., using the insulin calculator, communicating wirelessly with an insulin pump, etc.).

In some instances, the minimum threshold amount required to operate SCA 304 safely with minimal risk of abrupt shutdown may depend on historical usage of SCA 304. A user's previous history of usage may be used to determine an estimated minimum threshold requirement. For example, a user's previous usage may be tracked and used to determine an average usage and amount of power consumed in a period of time (e.g., days, hours, minutes, etc.).

In some instances, the threshold power consumption required by SCA 304 application may be estimated by tracking the usage history of the user. The usage history may account for specific events and the amount of power required for those events. For example, usage history may account for what features are accessed, how many times each feature is accessed, duration of use, etc. Example events for a SCA associated with analyte monitoring, such as glucose monitoring, may include, but are not limited to, strip measurements, insulin delivery measurements, insulin delivery, continuous glucose measurement readings, calibrations, etc. For instance, it may be determined that a user's average usage includes taking ten daily strip measurements, calculating and administering insulin five times a day, five Bluetooth communications per day, etc. A corresponding power consumption may then be determined. For example, it may be determined that SCA 304 requires a certain amount of milliamps per day, per hour, per week, etc., when SCA 304 is actively running. This power consumption determination may then be compared against the power capabilities determined for UDPD 200 to determine if UDPD 200 can meet the power threshold required for SCA 304. For example, if SCA 304 is used to receive CGM measurement readings derived from a sensor that is inserted every 5 days, then it can be determined if UDPD 200 has the necessary power capabilities to keep the CGM feature activated for the duration of time.

It is contemplated that in some instances various activities may be tracked individually to determine how much power is consumed per activity. In this way, a user's average usage can be tallied up per activity to come to an average power consumption amount. In some instances, a programmed therapy program can be implemented (e.g., by a physician) and a minimum power consumption threshold tallied up based on the customized program. It has been further contemplated that multiple user profiles may be created and used—e.g., a profile for average daily usage requirements, profiles for custom therapy programs, a profile specific to periods of continuous glucose monitoring, etc. It should also be understood that in some instances, the power consumption per activity may be determined in manufacturing and testing—e.g., for different types of UDPDs—and stored as reference data.

At block 1615, a determination whether UDPD 200 has sufficient power capabilities to run SCA 304 safely with minimal risk of abrupt shutdown is made based on the comparison of the power capabilities of UDPD 200 to any minimum threshold amounts required. If the required thresholds are not met, then SCA 304 is prevented from operating freely, represented by block 1620. Again, this may include, for example, SCA 304 being disabled and prevented from running on UDPD 200, SCA 304 permitted to operate but without the use of the safety critical features or capabilities, etc. This may also include, in some instances, permitting SCA 304 to operate without the functions for which the thresholds are not met.

In some embodiments, a determination that SCA 304 operates properly requires at least that the UDPD have sufficient power capabilities to operate safely with minimal risk of shutdown. If UDPD 200 has at least the minimum threshold of power capability, then at block 1625, UDPD 200 is determined to have sufficient power capability. SCA 304 is determined to operate properly on UDPD 200 and permitted to operate freely on UDPD 200, as long as any other required checks performed, or required to be performed, are successfully passed as well.

It is also contemplated that in some instances the power management check may be initiated to determine if the power capabilities of UDPD 200 are as expected. For example, average consumption rates for different types of UDPDs running SCA 304 may be determined during manufacturing and testing and stored as reference data. Thereafter, during use by the user, the power management check may monitor the power consumption rates of UDPD 200 while running SCA 304. If the results vary from the reference data more than a predetermined threshold deviation, then the power management check indicates that SCA 304 is not operating properly on UDPD 200, and thus SCA 304 is prevented from operating freely. For example, it may be determined during manufacturing and testing that the iPhone® can operate SCA 304 for 8 hours without recharge. If the power management check is run after installed on a user's UDPD 200, and results in an estimated 2 hours without recharge, this may be indicative of issues on the device that may compromise the safety critical features of the device. For instance, major deviations in expected consumption rates may be indicative of software bugs or viruses. In such case, for example, SCA 304 may be prevented from operating freely and the user informed of, or prompted to address, the problem (e.g., prompted to run a virus scan of the device).

The power management check may be programmed to initiate at various times—e.g., runtimes and/or non-runtimes. For example, the power management check may be programmed to initiate every time before SCA 304 is run, periodically after a predetermined amount of time, whenever the software environment has changed, etc.

In some embodiments, the power management check may be initiated as part of the installation process. For example, in FIG. 11, the power management check may be initiated before, after, or simultaneously with functional check 1130 in process 1100. Therefore, in addition to expected results for the installation check and functional check, block 1155 would also require expected results for the power management check (e.g., that the UDPD has sufficient power capability to run the SCA safely). If the power management check results in unexpected results (e.g., the UDPD does not have sufficient power capability to run the SCA safely), then SCA 304 is prevented from operating freely. Thus, process 1100 would determine if SCA 304 installed correctly, if UDPD 200 has sufficient power capability to run SCA 304 safely, and if SCA 304 functions properly. It should be understood that additional checks may also be included—e.g., the host integrity check, coexistence check, interoperability check, etc.

In some embodiments, the power management check may be programmed to initiate when the software environment has changed. For example, in FIG. 12, the power management check may be initiated before, after, or simultaneously with functional check 1225 in process 1200. Therefore, in addition to a expected results for the functional check, block 1245 would also require expected results for the power management check (e.g., that the UDPD has sufficient power capability to run the SCA safely). If the power management check results in unexpected results (e.g., the UDPD does not have sufficient power capability to run SCA 304 safely), then SCA 304 is prevented from operating freely. Thus, process 1200 would determine if the environment changed, if the UDPD has sufficient power capability to run SCA 304 safely, and if SCA 304 still functions properly. It should be understood that additional checks may also be included—e.g., the host integrity check, coexistence check, interoperability check, etc.

Throughout the foregoing description, for the purposes of explanation, numerous specific details were set forth in order to provide a thorough understanding of the invention. It will be apparent, however, to one skilled in the art that the invention may be practiced without some of these specific details. In addition, embodiments of the invention may include various operations as set forth above, or fewer operations or more operations, or operations in an order which is different from the order described herein. Accordingly, the scope and spirit of the invention should be judged in terms of the claims which follow as well as the legal equivalents thereof.

It should be understood that techniques introduced in the preceding can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-readable medium can be used to store software instructions, which when executed by a processor, causes the processor to perform the various methods of this description. A machine-readable medium includes recordable/non-recordable media (e.g., read-only memory (ROM); random access memory (RAM); magnetic disk storage media; optical storage media; flash memory devices; etc.), or any type of media suitable for storing machine-readable instructions. The term "logic", as used herein, can include, for example, special purpose hardwired circuitry, software and/or firmware in conjunction with programmable circuitry, or a combination thereof.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A method for hosting a safety critical application for glucose monitoring on an uncontrolled data processing device, the uncontrolled data processing device being configured to permit a user to make software and/or hardware changes to the uncontrolled data processing device and being configured for data communication with a continuous in vivo glucose monitoring device including an in vivo glucose sensor for providing measurement data related to the user's glucose, wherein the in vivo glucose monitoring device is configured to process the measurement data from the analyte sensor, the method comprising:

determining, with an uncontrolled data processing device, whether a safety critical application is installed properly and/or functions properly on the uncontrolled data processing device, the safety critical application configured for receiving the processed measurement data from the continuous in vivo glucose monitoring device and performing glucose monitoring;

preventing, with the uncontrolled data processing device, the safety critical application from operating on the uncontrolled data processing device upon verification that the safety critical application did not install properly or does not function properly on the uncontrolled data processing device; and permitting, with the uncontrolled data processing device, the safety critical application to operate freely on the uncontrolled data processing device upon verification that the safety critical application is installed properly and/or functions properly on the uncontrolled data processing device, wherein the safety critical application is a medically-related application and the uncontrolled data processing device is a wireless personal device comprising a display.

2. The method according to claim 1, wherein the in vivo glucose sensor comprises a partially implanted glucose sensor.

3. The method according to claim 1, wherein the uncontrolled data processing device comprises a handheld data processing device.

4. The method according to claim 3, wherein the uncontrolled data processing device comprises a mobile telephone.

5. The method according to claim 1, wherein the preventing of the SCA from operating on the UDPD comprises disabling, with the UDPD, the SCA from being run on the UDPD.

6. The method of claim 5, wherein the determining whether the SCA functions properly on the UDPD comprises:
   initiating, with the UDPD, an image to be displayed on a display of the UDPD, the image in the form of a verification inquiry;
   receiving, with the UDPD, user input in response to the verification inquiry; and
   comparing, with the UDPD, the user input received with reference display data.

7. The method according to claim 6, wherein the determining whether the SCA functions properly on the UDPD comprises: determining, with the UDPD, whether the SCA communicates properly on the UDPD with an external device.

8. The method according to claim 7, wherein determining whether the safety critical application is installed properly and/or functions properly on the uncontrolled data processing device comprises performing at least one of an installation check, a functional check, an environment check, a host integrity check, a coexistence check, an interoperability check and a power management check.

9. The method according to claim 6, wherein determining whether the safety critical application is installed properly and/or functions properly on the uncontrolled data processing device comprises performing at least one of an installation check, a functional check, an environment check, a host integrity check, a coexistence check, an interoperability check and a power management check.

10. The method according to claim 5, wherein the determining whether the SCA functions properly on the UDPD comprises: determining, with the UDPD, whether the SCA communicates properly on the UDPD with an external device.

11. The method according to claim 10, wherein determining whether the safety critical application is installed properly and/or functions properly on the uncontrolled data processing device comprises performing at least one of an installation check, a functional check, an environment check, a host integrity check, a coexistence check, an interoperability check and a power management check.

12. The method according to claim 5, wherein determining whether the safety critical application is installed properly and/or functions properly on the uncontrolled data processing device comprises performing at least one of an installation check, a functional check, an environment check, a host integrity check, a coexistence check, are interoperability check and a power management check.

13. The method according to claim 1, wherein the determining whether the SCA functions properly on the UDPD comprises:
   initiating, with the UDPD, an image to be displayed on a display of the UDPD, the image in the form of a verification inquiry;
   receiving, with the UDPD, user input in response to the verification inquiry; and
   comparing, with the UDPD, the user input received with reference display data.

14. The method according to claim 13, wherein the determining whether the SCA functions properly on the UDPD comprises: determining, with the UDPD, whether the SCA communicates properly on the UDPD with an external device.

15. The method according to claim 14, wherein determining whether the safety critical application is installed properly and/or functions properly on the uncontrolled data processing device comprises performing at least one of an installation check, a functional check, an environment check, a host integrity check, a coexistence check, an interoperability check and a power management check.

16. The method according to claim 13, wherein determining whether the safety critical application is installed properly and/or functions properly on the uncontrolled data processing device comprises performing at least one of an installation check, a functional check, an environment check, a host integrity check, a coexistence check, an interoperability check and a power management check.

17. The method according to claim 1, wherein the determining whether the SCA functions properly on the UDPD comprises: determining, with the UDPD, whether the SCA communicates properly on the UDPD with an external device.

18. The method according to claim 17, wherein determining whether the safety critical application is installed properly and/or functions properly on the uncontrolled data processing device comprises performing at least one of an installation check, a functional check, an environment check, a host integrity check, a coexistence check, an interoperability check and a power management check.

19. The method according to claim 1, wherein determining whether the safety critical application is installed properly and/or functions properly on the uncontrolled data processing device comprises performing at least one of an installation check, a functional check, an environment check, a host integrity check, a coexistence check, an interoperability check and a power management check.

20. A non-transitory computer-readable medium storing a computer program comprising a safety critical application for glucose monitoring configured for installation on an uncontrolled data processing device, the uncontrolled data processing device being configured to permit a user to make software and/or hardware changes to the uncontrolled data processing device and being configured for data communication with a continuous in vivo monitoring device including an in vivo glucose sensor for providing measurement data related to the user's glucose, wherein the in vivo glucose monitoring device is configured to process the measurement data from the analyte sensor, the computer program comprising instructions that, when executed by the uncontrolled data processing device, cause the uncontrolled data processing device to implement the steps of:
   determining whether the safety critical application is installed properly and/or functions properly on the uncontrolled data processing device, the safety critical application being configured to receive the processed measurement data from the continuous in vivo glucose monitoring device and perform analyte monitoring;
   preventing the safety critical application from operating on the uncontrolled data processing device upon verification that the safety critical application did not install properly or does not function properly on the uncontrolled data processing device; and
   permitting the safety critical application to operate freely on the uncontrolled data processing device upon verification that the safety critical application is installed properly and/or functions properly on the uncontrolled data processing device, wherein the safety critical application is a medically-related application and the uncontrolled data processing device is a wireless personal device comprising a display.

\* \* \* \* \*